US012595343B2

(12) United States Patent
Villeneuve et al.

(10) Patent No.: US 12,595,343 B2
(45) Date of Patent: Apr. 7, 2026

(54) ADDITIVE MIXTURES FOR RHEOLOGY MODIFICATION OF POLYMERS

(71) Applicant: BASF SE, Ludwigshafen am Rhein (DE)

(72) Inventors: Sebastien Villeneuve, Kaisten (CH); Peter Nesvadba, Schweizerhalle (CH); Daniel Mueller, Kaisten (CH); Raphael Dabbous, Kaisten (CH)

(73) Assignee: BASF SE, Ludwigshafen am Rhein (DE)

( * ) Notice: Subject to any disclaimer, the term of this patent is extended or adjusted under 35 U.S.C. 154(b) by 833 days.

(21) Appl. No.: 17/905,018

(22) PCT Filed: Feb. 24, 2021

(86) PCT No.: PCT/EP2021/054503
§ 371 (c)(1),
(2) Date: Aug. 25, 2022

(87) PCT Pub. No.: WO2021/170615
PCT Pub. Date: Sep. 2, 2021

(65) Prior Publication Data

US 2023/0272171 A1 Aug. 31, 2023

(30) Foreign Application Priority Data

Feb. 26, 2020 (EP) .................................... 20159546

(51) Int. Cl.

| | |
|---|---|
| ***C08J 3/22*** | (2006.01) |
| ***C07C 265/14*** | (2006.01) |
| ***C07C 333/00*** | (2006.01) |
| ***C07D 251/32*** | (2006.01) |
| ***C07D 491/113*** | (2006.01) |
| ***C08K 5/205*** | (2006.01) |
| ***C08K 5/3467*** | (2006.01) |
| ***C08K 5/372*** | (2006.01) |
| ***C08K 5/43*** | (2006.01) |
| ***D01D 5/38*** | (2006.01) |
| ***D04H 3/007*** | (2012.01) |
| ***D04H 3/16*** | (2006.01) |

(52) U.S. Cl.
CPC ............. *C08J 3/226* (2013.01); *C07C 265/14* (2013.01); *C07C 333/00* (2013.01); *C07D 251/32* (2013.01); *C07D 491/113* (2013.01); *C08K 5/205* (2013.01); *C08K 5/3467* (2013.01); *C08K 5/3725* (2013.01); *C08K 5/43* (2013.01); *D01D 5/38* (2013.01); *D04H 3/007* (2013.01); *D04H 3/16* (2013.01); *C08J 2479/04* (2013.01); *D10B 2321/022* (2013.01)

(58) Field of Classification Search
CPC ..... C08J 3/226; C08J 2479/04; C07C 264/14; C07C 333/00; C07D 251/32; C07D 491/113; C07D 493/10; C08K 5/205; C08K 5/3467; C08K 5/34; C08K 5/3435; C08K 5/39; C08L 23/04; C08L 23/10
USPC .......................................................... 523/351
See application file for complete search history.

(56) References Cited

U.S. PATENT DOCUMENTS

| | | | |
|---|---|---|---|
| 4,325,863 A | 4/1982 | Hinsken et al. | |
| 4,338,244 A | 7/1982 | Hinsken et al. | |
| 4,521,320 A | 6/1985 | Spivack et al. | |
| 4,546,148 A | 10/1985 | Cantatore | |
| 5,175,312 A | 12/1992 | Dubs et al. | |
| 5,216,052 A | 6/1993 | Nesvadba et al. | |
| 5,252,643 A | 10/1993 | Nesvadba | |
| 5,356,966 A | 10/1994 | Nesvadba | |
| 5,367,008 A | 11/1994 | Nesvadba | |
| 5,428,162 A | 6/1995 | Nesvadba | |
| 5,428,177 A | 6/1995 | Nesvadba | |
| 5,488,117 A | 1/1996 | Nesvadba | |
| 9,902,871 B2 | 2/2018 | Steinbrecher et al. | |
| 10,240,268 B2 | 3/2019 | Novarino et al. | |
| 2003/0216494 A1 | 11/2003 | Roth et al. | |
| 2004/0077817 A1 | 4/2004 | Wamprecht et al. | |
| 2006/0141403 A1 | 6/2006 | Ramsden et al. | |
| 2007/0060697 A1 | 3/2007 | Li et al. | |
| 2008/0045662 A1 | 2/2008 | Roth et al. | |
| 2009/0111918 A1 | 4/2009 | Tsou et al. | |
| 2009/0192284 A1 | 7/2009 | Bruchmann et al. | |
| 2013/0145962 A1 | 6/2013 | Gupta et al. | |
| 2019/0323156 A1* | 10/2019 | Mueller | D04H 3/005 |
| 2019/0367666 A1 | 12/2019 | Tillack et al. | |

FOREIGN PATENT DOCUMENTS

| | | |
|---|---|---|
| CA | 1 225 654 A | 8/1987 |
| DE | 4316611 A1 | 11/1993 |
| DE | 4316622 A1 | 11/1993 |
| DE | 4316876 A1 | 11/1993 |
| EP | 0589839 A1 | 3/1994 |
| EP | 0591102 A1 | 4/1994 |
| EP | 1291384 A1 | 3/2003 |
| EP | 3034552 A1 | 6/2016 |
| EP | 2 978 788 B1 | 11/2017 |
| GB | 701712 A | 12/1953 |
| JP | 60-109559 A | 6/1985 |
| JP | 2017- 508082 A | 3/2017 |

(Continued)

OTHER PUBLICATIONS

What's the difference between LDPE, LLDPE, MDPE, HDPE, XLPE and UHMW sheeting? United States Plastic Corporation, pp. 1-3, Published Aug. 13, 2008. (Year: 2008).*

(Continued)

*Primary Examiner* — Hannah J Pak
(74) *Attorney, Agent, or Firm* — Grüneberg Global IP, PLLC

(57) ABSTRACT

A mixture can be used for modifying the rheology of polymeric substrates. The mixture contains a hydroxylamine ester and an isocyanate functionalized with a thio compound.

18 Claims, No Drawings

(56) References Cited

FOREIGN PATENT DOCUMENTS

| | | | |
|---|---|---|---|
| WO | WO-01/90113 | A1 | 11/2001 |
| WO | WO-2005/070987 | A1 | 8/2005 |
| WO | 2016/096690 | A1 | 6/2016 |

OTHER PUBLICATIONS

Noble et al., "Mechanistic Insights into N-Acyloxyamine-Initiated Controlled Degradation of Polypropylene: The Unexpected Role of Keto-Enol Tautomerization in Carboxylate Radical Chemistry", The Journal of Organic Chemistry, vol. 85, Dec. 20, 2019, pp. 2338-2346.

European Search Report for EP Patent Application No. 20159546.9, Issued on Sep. 16, 2020, 3 pages.

Fahrbach, et al., "Chapter: 2.1 Fibers", Nonwoven Fabrics, Ullmann's Encyclopedia of Industrial Chemistry, vol. 24, ed. Ley, et al., Jun. 15, 2000, pp. 586-589.

International Search Report for PCT Patent Application No. PCT/EP2021/054503, Issued on Jun. 8, 2021, 4 pages.

Written Opinion for PCT Patent Application No. PCT/EP2021/054503, Issued on Jun. 8, 2021, 8 pages.

International Preliminary Report on Patentability for PCT/2021/054503, Issued Jun. 7, 2022, 20 pages.

Zhou et al., "Synthesis and application of a formaldehyde-free flame retardant for bamboo viscose fabric", Textile Research Journal, vol. 84, No. 14, Mar. 3, 2014, pp. 1515-1527.

Zhang et al., "Preparation and Properties of Toluene-Diisocyanate-Trimer-Modified Epoxy Resin", Polymers, vol. 11, Mar. 4, 2019, pp. 1-12.

* cited by examiner

ADDITIVE MIXTURES FOR RHEOLOGY MODIFICATION OF POLYMERS

CROSS-REFERENCE TO RELATED APPLICATIONS

This application is the National Stage entry under § 371 of International Application No. PCT/EP2021/054503, filed on Feb. 24, 2021, and which claims the benefit of priority to European Application No. 20159546.9, filed on Feb. 26, 2020, The content of each of these applications is hereby incorporated by reference in its entirety.

BACKGROUND OF THE INVENTION

Field of the Invention

The present invention relates to compositions comprising a polymeric substrate and a mixture of hydroxylamine esters with isocyanates which are functionalized with thio compounds, corresponding mixtures and the use of such mixtures for modifying the rheology of polymeric substrates. A further object of the present invention are novel isocyanates functionalized with thio compounds.

Description of Related Art

The controlled preparation of polymer types (polymer types having different molar masses, melt viscosities, densities, molar mass distributions, etc.) by customary compounding methods, for example by extrusion or injection moulding, is a routine process employed by polymer manufacturers and polymer processors/compounders.

The setting of the desired parameters, for example the melt viscosity, by means of this polymer process step is critically dependent on the controlled reactivity and mode of action of the additives employed.

The use of free-radical formers for modifying the melt viscosity (rheology) of polyolefins is a generally known method. Whether it results in a lowering of the molecular weight (degradation) or an increase in the molecular weight (crosslinking, branching) depends primarily on the chemical structure of the polyolefin.

The reaction of a polymer of the polypropylene type with a free-radical former during a polymer-processing process generally results in the degradation of the polymer, whereas polymers of the polyethylene type tend to crosslinking. Examples that may be mentioned here are polyethylene types, which are obtainable by means of Phillips catalysts (HDPE) or metallocene catalysts (LLDPE). Exceptions are the polyethylene types prepared by the Ziegler process, which likewise tend to undergo chain degradation when processed in the presence of free-radical formers.

In the case of copolymers and terpolymers or copolymer blends, high proportions of propylene produce polypropylene-like behaviour, while high proportions of ethylene result in polyethylene-like behaviour. If the above-mentioned copolymers and terpolymers or copolymer blends comprise proportions of multiply unsaturated olefins, the probability of crosslinking decreases with decreasing concentration of free double bonds.

The controlled degradation of polypropylene (PP) to give a product having a lower molecular weight and a narrower molecular weight distribution is a commercially important process for producing 'controlled rheology' polypropylene (CR-PP). While specific PP grades ("reactor grades") are obtainable by optimisation of the synthesis process or the catalyst systems (metallocene catalyst), standard PP grades are frequently modified in process technology by means of a processing step following the synthesis.

Known degradation processes proceed either thermally, in particular at temperatures above 280° C., or in the presence of free-radical generators. In process technology, the free-radical-induced process is carried out in extruders or injection-moulding machines at temperatures above 180° C. Suitable free-radical generators are organic peroxides which are added during the processing step in diluted form (PP masterbatch, or diluted in oil, or stabilized on organic or inorganic supports, or incorporated into porous organic carriers) or directly as a liquid. Under the given processing conditions, the peroxide dissociates disintegrates into free radicals, which initiate the chain cleavage reactions and form polymers having the desired rheological properties (melt viscosities). The controlled degradation of a PP to form a product having a lower molecular weight (higher melt flow rate (MFR)) is generally referred to as a viscosity-breaking or vis-breaking process.

CR-PP grades are mainly used for fibre applications and injection-moulding applications in which low melt viscosities are a prerequisite. A wide range of melt viscosities or molecular weights is nowadays required in order to have PP grades that can be processed in the many existing technologies.

A further parameter that influences the processing behaviour of the polymer, in addition to the molecular weight, is the molecular weight distribution (MWD). While polymer grades having broad MWDs display improved orientation behaviour of the polymer chains at low pull-off speeds in a fibre spinning process, the reverse is the case for high pull off speeds and broad MWDs. For this reason, narrow MWDs are essential at high pull-off speeds in order to achieve improved continuity in the spinning process. In addition, polymer grades with too broad MWDs tend to be more difficult to process as nonwovens (e.g. meltblown, spunbond processes) or the quality of the obtained properties of the nonwovens can be decreased.

The use of peroxides is a drawback, since only a restricted "processing temperature window" is available because of their decomposition temperatures, which are generally below the customary temperatures of polymer processing.

WO 01/90113 discloses a process for reducing the molecular weight of polypropylene, propylene copolymers or polypropylene blends, wherein a hydroxylamine ester is added to the polymers to be degraded.

SUMMARY OF THE INVENTION

The present invention relates to the problem of improving that prior art process further by lowering the process temperature and obtaining polymers of a more homogeneous (narrow) molecular weight distribution and a reduced level of oligomeric and volatile decomposition products.

It has now surprisingly been found that the combination of selected hydroxylamine esters and selected isocyanates which are functionalized with thio compounds shows a significant synergistic effect, which results in an excellent degradation performance even at low temperatures.

DETAILED DESCRIPTION OF THE INVENTION

The present invention relates to a composition comprising (a) a compound of formula (1) or (2)

(1)

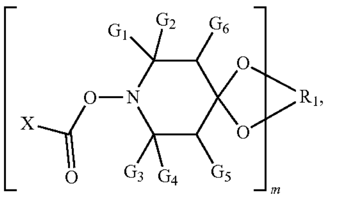

(2)

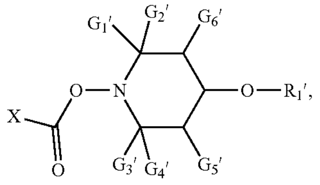

wherein $G_1$, $G_2$, $G_3$ and $G_4$ are each independently of the other $C_1$-$C_4$alkyl, or $G_1$ and $G_2$ together or $G_3$ and $G_4$ together are pentamethylene;

$G_1'$, $G_2'$, $G_3'$ and $G_4'$ are each independently of the other $C_1$-$C_4$alkyl, or $G_1'$ and $G_2'$ together or $G_3'$ and $G_4'$ together are pentamethylene;

$G_5$, $G_6$, $G_5'$ and $G_6'$ are each independently of the other hydrogen or $C_1$-$C_4$alkyl; and X and X' are independently of each other hydrogen, $C_1$-$C_{18}$alkyl, $C_2$-$C_{18}$alkenyl, —O—$C_1$-$C_{18}$alkyl, —NH—$C_1$-$C_{18}$alkyl, —N($C_1$-$C_6$alkyl$)_2$, phenyl, phenoxy or —NH-phenyl, m is 1 or 2, and when m is 1, $R_1$ is $C_2$-$C_8$alkylene or $C_2$-$C_8$hydroxyalkylene or $C_4$-$C_{36}$acyloxyalkylene, or, when m is 2, $R_1$ is $(—CH_2)_2C(CH_2—)_2$, and $R_1'$ is hydrogen, $C_1$-$C_8$alkyl, $C_1$-$C_8$hydroxyalkyl or a group of formula —(C═O)—$C_1$-$C_{40}$alkyl, or —O—$R_1'$ together with the —CH— group linking them are the group —(C═O)—, (b) a compound of formula (3)

$$A-[S-R]_n, \quad (3)$$

wherein

A is based on an organic isocyanate, wherein the radical (s) —S—R are introduced by reaction with isocyanate groups, R is $C_2$-$C_{40}$alkyl which is optionally substituted and/or interrupted, and n is equal to or greater than 1, and (c) a polymeric substrate.

Examples of any substituents that are $C_1$-$C_4$alkyl or $C_1$-$C_8$alkyl are methyl, ethyl, n-propyl, n-butyl, sec-butyl or tert-butyl.

Examples of any substituents that are $C_1$-$C_{18}$alkyl are methyl, ethyl, n-propyl, n-butyl, sec-butyl, tert-butyl, n-hexyl, n-octyl, 2-ethyl-hexyl, n-nonyl, n-decyl, n-undecyl, n-dodecyl, n-tridecyl, n-tetradecyl, n-hexadecyl, n-heptadecyl or n-octadecyl.

Examples of any substituents that are $C_2$-$C_{18}$alkenyl are 1-propenyl, allyl, methallyl, 2-butenyl, 2-pentenyl, 2-hexenyl, 2-octenyl or 4-tert-butyl-2-butenyl.

Examples of any substituents that are —O—$C_1$-$C_{18}$alkyl are corresponding substituents wherein $C_1$-$C_{18}$alkyl is as given above.

Examples of any substituents that are —NH—$C_1$-$C_{18}$alkyl are corresponding substituents wherein $C_1$-$C_{18}$alkyl is as given above.

Examples of any substituents that are —N($C_1$-$C_6$alkyl$)_2$ are corresponding substituents wherein the $C_1$-$C_6$alkyl radicals are independently from each other methyl, ethyl, n-propyl, n-butyl, sec-butyl or tert-butyl, like $—N(CH_3)_2$ or $—N(C_2H_5)_2$.

Phenyl, phenoxy and —NH-phenyl can be unsubstituted or substituted by $C_1$-$C_4$alkyl, preferably by methyl.

Examples of any substituents that are $C_2$-$C_8$alkylene are ethylene, propylene, 2,2-dimethylpropylene, tetramethylene, hexamethylene or octamethylene. Examples of $C_2$-$C_8$hydroxyalkylene are the corresponding radicals given above for $C_2$-$C_8$alkylene, which are substituted by one or two, especially by one, hydroxyl radical.

$C_4$-$C_{36}$acyloxyalkylene is preferably $C_1$-$C_{20}$acyloxy-$C_3$-$C_{10}$alkylene. Examples of any substituents that are $C_4$-$C_{36}$acyloxyalkylene are groups of the formula (4)

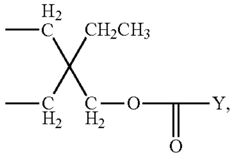

wherein Y is $C_1$-$C_{20}$alkyl, like the group of formula (4a)

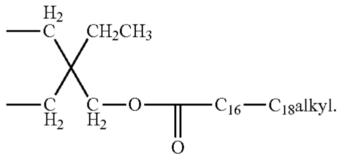

Examples of $C_1$-$C_8$hydroxyalkyl are methyl, ethyl, n-propyl, n-butyl, sec-butyl, tert-butyl, n-hexyl, n-octyl and 2-ethyl-hexyl which are substituted by one or two, especially by one, hydroxyl radical.

A group of formula —(C═O)—$C_1$-$C_{40}$alkyl is preferably —(C═O)—$C_1$-$C_{20}$alkyl, especially —(C═O)—$C_{16}$-$C_{18}$alkyl.

$G_1$, $G_2$, $G_3$ and $G_4$, as well as $G_1'$, $G_2'$, $G_3'$ and $G_4'$, are preferably $C_1$-$C_4$alkyl, especially methyl or ethyl. More preferably, $G_1$, $G_3$, $G_1'$ and $G_3'$ are methyl and $G_2$, $G_4$, $G_2'$ and $G_4'$ are ethyl.

$G_5$, $G_6$, $G_5'$ and $G_6'$ are preferably hydrogen or methyl. More preferably, $G_5$ and $G_5'$ are hydrogen and $G_6$ and $G_6'$ are methyl.

X and X' are preferably hydrogen, $C_1$-$C_{18}$alkyl, —O—$C_1$-$C_{18}$alkyl, —NH—$C_1$-$C_{18}$alkyl or —N($C_1$-$C_6$alkyl)$_2$, especially hydrogen or $C_1$-$C_{18}$alkyl. More preferably, X and X are $C_1$-$C_4$alkyl, especially methyl.

In compound of formula (1) it is preferred that n is 1.

Furthermore, in compound of formula (1) it is preferred that n is 1 and $R_1$ is $C_2$-$C_8$alkylene or $C_4$-$C_{36}$acyloxyalkylene, especially $C_4$-$C_{36}$acyloxyalkylene. More preferably n is 1 and $R_1$ is a compound of formula (4), especially a compound of formula (4a).

$R_1$' is preferably a group of formula —(C═O)—$C_1$-$C_{40}$alkyl, more preferably —(C═O)—$C_1$-$C_{20}$alkyl, especially —(C═O)—$C_{16}$-$C_{18}$alkyl.

Highly preferred as compound of formula (1) is the compound of formula (5)

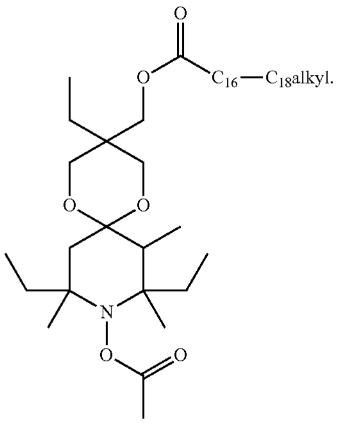

The compounds of formula (5) usually comprise mixtures of $C_{16}$-$C_{18}$ alkyl radicals, but may also contain only one of the alkyl radicals.

It is preferred that component (a) is a compound of formula (1), for which the above preferences apply.

More preferably, component (a) is a compound of formula (1), wherein n is 1 and $R_1$ is $C_4$-$C_{36}$acyloxyalkylene.

It is highly preferred that component (a) is a compound of formula (5).

Compounds of formulae (1) and (2) are known or can be prepared according to known methods, for example as given in WO 01/90113.

A is preferably based on an organic isocyanate, which is a cyclohexyl diisocyanate, methylenebis(cyclohexyl) diisocyanate, isophorone diisocyanate, phenyl diisocyanate, diphenylmethane diisocyanate or naphthyl diisocyanate each of which is unsubstituted or substituted by $C_1$-$C_4$alkyl or di($C_1$-$C_4$alkyl)amino, or is $C_4$-$C_{20}$alkyl diisocyanate, or an oligomeric or polymeric product obtained by reaction of the above diisocyanates with themselves and/or with a polyol.

More preferably, A is based on an organic isocyanate, which is a phenyl diisocyanate, diphenylmethane diisocyanate or naphthyl diisocyanate each of which is unsubstituted or substituted by $C_1$-$C_4$alkyl or di($C_1$-$C_4$alkyl)amino, or an oligomeric or polymeric product obtained by reaction of the above diisocyanates with themselves and/or with a polyol.

It is highly preferred that A is based on an organic isocyanate, which is a phenyl diisocyanate which is unsubstituted or substituted by $C_1$-$C_4$alkyl, or an oligomeric or polymeric product obtained by reaction of the above diisocyanates with themselves and/or with a polyol.

It is most preferred that A is based on toluene-2,4-diisocyanate or toluene-2,6-diisocyanate, or an oligomeric or polymeric product obtained by reaction of the above diisocyanates with themselves and/or with a polyol.

Examples of products obtained by reaction of the above diisocyanates with themselves are the following reaction products of three equivalents of toluene-2,4-diisocyanate or toluene-2,6-diisocyanate, respectively:

(6)

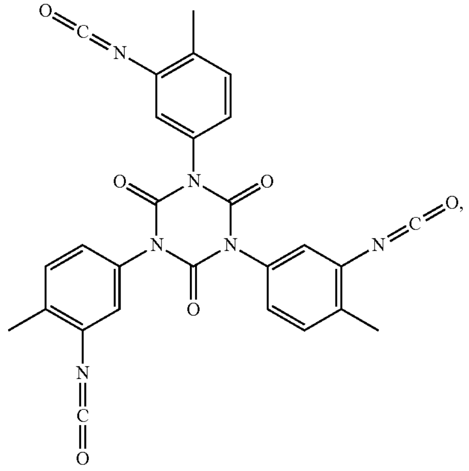

(7)

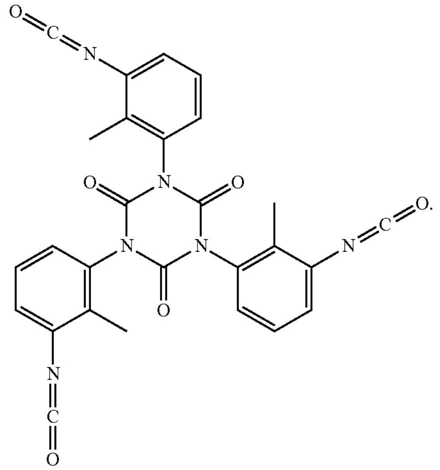

Examples of products obtained by reaction of the above diisocyanates with polyols are the following reaction products of toluene-2,4-diisocyanate or toluene-2,6-diisocyanate, respectively, with a polyol of formula HO—$CH_2$—C($CH_2$—OH)$_2$—$CH_2$—$CH_3$:

(8)

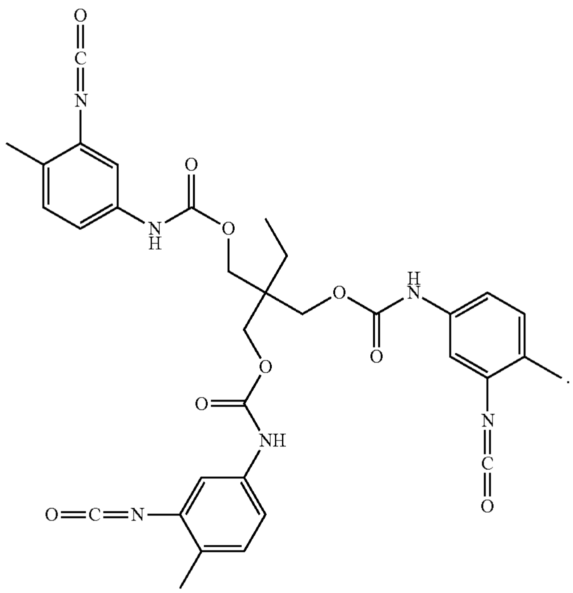

(9)

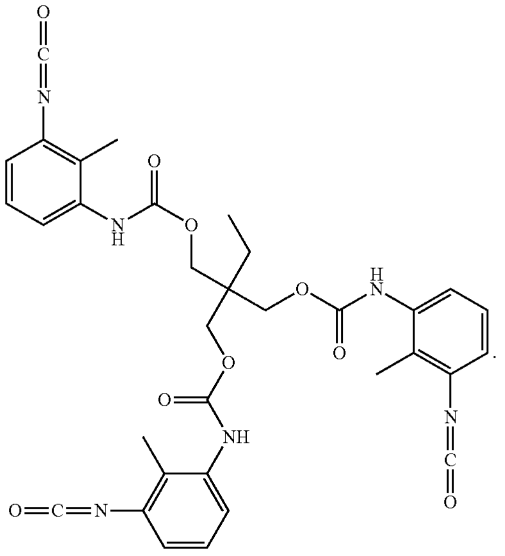

A polyol is preferably $C_1$-$C_{10}$alkanol comprising two or more hydroxy groups, or a poly-$C_2$-$C_{10}$alkylene glycol.

Preferred as $C_1$-$C_{10}$alkanol for the polyols are those which are substituted by two to four, especially two or three, hydroxy groups. Particularly preferred is $C_2$-$C_{10}$alkanol, especially $C_2$-$C_6$alkanol, which are correspondingly substituted by hydroxy groups. Highly preferred is the polyol of formula $HO—CH_2—C(CH_2—OH)_2—CH_2—CH_3$.

Preferred as poly-$C_2$-$C_{10}$alkylene glycol is poly-$C_2$-$C_6$alkylene glycol, especially those of formula $$H-\left[O-C_2-C_6\text{alkylene}\right]_y-OH, \quad (10)$$

wherein y is a number from 2 to 600, especially from 2 to 200 and most preferably from 2 to 100.

Highly preferred is a number from 2 to 50, especially 2 to 20.

As to formula (10), preference is given to corresponding polyethylene glycol or polypropylene glycol.

Preferably, the polyol is $C_2$-$C_6$alkanol, which is substituted by two to four hydroxy groups, or poly-$C_2$-$C_6$alkylene glycol, especially such of formula (10).

In case of a reaction of the diisocyanates with themselves, or the reaction of different types of diisocyanates with themselves, this can result in mixtures of different oligomers or polymers, and in case of the additional reaction with polyols even more complex mixtures can be obtained.

Corresponding organic isocyanates are known or can be obtained according to known processes, for example from WO 05/070987.

R can, for example, be interrupted by —O—, —NH—, —S— and/or a carbonyl group. A possible substituent for R is —SH. Corresponding $C_8$-$C_{40}$alkyl, especially $C_8$-$C_{20}$alkyl, is preferred.

R is preferably $C_2$-$C_{40}$alkyl which is uninterrupted or interrupted by —O—, —NH—, —S— and/or a carbonyl group, especially by —O— and/or a carbonyl group.

Particularly preferably R is $C_8$-$C_{40}$alkyl, especially $C_8$-$C_{20}$alkyl, which is uninterrupted or interrupted by —O— and/or a carbonyl group.

Compounds of formula (3) are obtainable by reaction of an organic isocyanate with thiols of formula $$H—S—R \quad (11),$$

wherein for R the above definitions and preferences apply.

The radical(s) —S—R are introduced by reaction with isocyanate groups of the organic isocyanate, and in the reaction product are bonded as groups of formula (12)

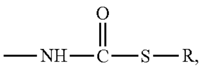

wherein R is as defined above.

In view of the above, the term "isocyanates functionalized with thio compounds" relates to corresponding thiourethanes.

The above process for the preparation of the compounds of formula (3) is, as a rule, carried out in presence of catalysts, like tertiary amines, for example triethylene diamine, dimethylpiperazine, dimethylethanolamine, 1,4-diazabicyclo[2.2.2]octane or 1,8-diazabicyclo[5,4,0]undec-7-ene, or with tin compounds as catalysts, for example dibutyl tin dilaurate. Triethylamine is preferred. The catalyst is, for example, used in an amount of 0.1 to 10 weight-%, based on the weight of the organic isocyanate.

The reaction is usually carried out in presence of an organic solvent, like tetrahydrofuran or ethyl acetate, and at temperatures of, for example 30 to 80° C.

Preferably component (c), the polymeric substrate, is a thermoplastic polymer. More preferably, the polymeric substrate is a polyolefin, polyester, polyamide, polyvinyl chloride, polyimide, polyacrylonitrile, polycarbonate or polystyrene polymer, especially a polyolefin.

Examples of polymers of olefins are monoolefins and diolefins, for example polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE). Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).
b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

Examples of mixtures of polyolefins are mixtures of polypropylene with polyisobutylene, polypropylene with polyethylene (for example PP/HDPE, PP/LDPE) and mixtures of different types of polyethylene (for example LDPE/HDPE).

Examples of copolymers of monoolefins and diolefins with each other or with other vinyl monomers, are ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is generated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylenevinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

It is preferred that the polymeric substrate is a thermoplastic polymer, preferably a polyolefin.

More preferably, the polymeric substrate is a polyolefin selected from the group consisting of polyethylene, like linear low density polyethylene, low density polyethylene, medium density polyethylene and high density polyethylene, and polyethylene copolymers and polypropylene homopolymers and polypropylene copolymers.

Highly preferred is polyethylene or polypropylene.

It is preferred that each compound of the present composition is present in the polymeric substrate (c) in an amount of 0.0001 to 5% by weight, especially 0.001 to 5% by weight and more preferably 0.01 to 5% by weight, based on the weight of the polymeric substrate Highly preferred is an amount of 0.01 to 2% by weight, especially 0.01 to 1% by weight.

The composition according to the present invention may additionally also contain various conventional additives, for example:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl) adipate.

1.4. Tocopherols, for example α-tocopherol, β-tocopherol, γ-tocopherol, 6-tocopherol and mixtures thereof (vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl] terephthalate, 1,1-bis-(3,5-dimethyl-2-hydroxyphenyl) butane, 2,2-bis(3,5-di-tert-butyl-4-hydroxyphenyl) propane, 2,2-bis(5-tert-butyl-4-hydroxy-2-methylphenyl)-4-n-dodecylmercaptobutane, 1,1,5,5-tetra-(5-tert-butyl-4-hydroxy-2-methylphenyl)pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl) sulfide, isooctyl-3,5-di-tert-butyl-4-hydroxybenzylmercaptoacetate.

1.8. Hydroxybenzylated malonates, for example dioctadecyl-2,2-bis(3,5-di-tert-butyl-2-hydroxybenzyl)malonate, di-octadecyl-2-(3-tert-butyl-4-hydroxy-5-methylbenzyl)malonate, di-dodecylmercaptoethyl-2,2-bis(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl) isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-ditert-butyl-4-hydroxyphenyl)carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane; 3,9-bis[2-{3-(3-tert-butyl-4-hydroxy-5-methylphenyl)propionyloxy}-1,1-dimethylethyl]-2,4,8,10-tetraoxaspiro[5.5]undecane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl) trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl] oxamide (Naugard®XL-1, supplied by Addivant).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl) diphenylamine, N,N-dimethyl-N,N-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl) amino]ethane, 1,2-bis(phenylamino)propane, (o-tolyl) biguanide, bis[4-(1',3'-dimethylbutyl)phenyl]amine, tert-octylated N-phenyl-1-naphthylamine, a mixture of monoand dialkylated tert-butyl/tert-octyldiphenylamines, a mixture of mono- and dialkylated nonyldiphenylamines, a mixture of mono- and dialkylated dodecyldiphenylamines, a mixture of monoand dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tertoctyl-phenothiazines, N-allylphenothiazine, N,N,N',N'-tetraphenyl-1,4-diaminobut-2-ene.

2. UV Absorbers and Light Stabilizers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl) benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl) benzotriazole, 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl) phenyl)benzotriazole, 2-(3'-tert-butyl-5'-[2-(2-ethylhexyloxy)carbonylethyl]-2'-hydroxyphenyl) benzotriazole, 2-(3'-dodecyl-2'-hydroxy-5'-methylphenyl)benzotriazole, 2-(3'-tert-butyl-2'-hydroxy-5'-(2-isooctyloxycarbonylethyl) phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300;

$$[R-CH_2CH_2-COO-CH_2CH_2]_2,$$

where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)-phenyl]benzotriazole; 2-[2'-hydroxy-3'-(1,1,3,3-tetramethylbutyl)-5'-(α,α-dimethylbenzyl)-phenyl] benzotriazole.

2.2. 2-Hydroxybenzophenones, for example the 4-hydroxy, 4-methoxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example 4-tert-butyl-phenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxy-cinnamate, methyl α-carbomethoxy-p-methoxycinnamate, N-(β-carbomethoxy-β-cyanovinyl)-2-methylindoline, neopentyl tetra(α-cyano-β,β-diphenylacrylate.

2.5. Nickel compounds, for example nickel complexes of 2,2'-thio-bis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenylundecylketoxime, nickel complexes of 1-phenyl-4-lauroyl-5-hydroxypyrazole, with or without additional ligands.

2.6. Sterically hindered amines, for example carbonic acid bis(1-undecyloxy-2,2,6,6-tetramethyl-4-piperidyl)ester, bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butanetetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensate of N,N'-bis(2,2,6,6-tetramethyl-4-piperidyl)hexamethylenediamine and 4-cyclohexylamino-2,6-dichloro-1,3,5-triazine, a condensate of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); a condensate of 1,6-hexanediamine and 2,4,6-trichloro-1,3,5-triazine as well as N,N-dibutylamine and 4-butylamino-2,2,6,6-tetramethylpiperidine (CAS Reg. No. [192268-64-7]); N-(2,2,6,6-tetramethyl-4-piperidyl)-n-dodecylsuccinimide, N-(1,2,2,6,6-pentamethyl-4-piperidyl)n-dodecylsuccinimide, 2-undecyl-7, 7,9,9-tetramethyl-1-oxa-3,8-diaza-4-oxo-spiro[4,5] decane, a reaction product of 7,7,9,9-tetramethyl-2-cycloundecyl-1-oxa-3,8-diaza-4-oxospiro-[4,5]decane and epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl)hexamethylenediamine, a diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, a reaction product of maleic acid anhydride-α-olefin copolymer with 2,2,6,6-tetramethyl-4-aminopiperidine or 1,2,2,6,6-pentamethyl-4-aminopiperidine, 2,4-bis[N-(1-cyclohexyloxy-2,2,6,6-tetramethylpiperidine-4-yl)-N-butylamino]-6-(2-hydroxyethyl)amino-1,3,5-triazine, 1-(2-hydroxy-2-methylpropoxy)-4-octadecanoyloxy-2,2,6,6-tetramethylpiperidine, 5-(2-ethylhexanoyl)oxymethyl-3,3,5-trimethyl-2-morpholinone, Hostavin® 3058 (Clariant; CAS Reg. No. 106917-31-1], 5-(2-ethylhexanoyl)oxymethyl-3,3,5-trimethyl-2-morpholinone, the reaction product of 2,4-bis[(1-cyclohexyloxy-2,2,6,6-piperidine-4-yl)butylamino]-6-chloro-s-triazine with N,N'-bis(3-aminopropyl)ethylenediamine), 1,3,5-tris(N-cyclohexyl-N-(2,2,6,6-tetramethylpiperazine-3-one-4-yl)amino)-s-triazine, 1,3,5-tris(N-cyclohexyl-N-(1,2,2,6,6-pentamethylpiperazine-3-one-4-yl)amino)-s-triazine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy)phenyl]-4,6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine, 2,4-bis(4-[2-ethylhexyloxy]-2-hydroxyphenyl)-6-(4-methoxyphenyl)-1,3,5-triazine, 2,4-bis(4-biphenylyl)-6-[2-hydroxy-4-(2-ethylhexyloxy)phenyl]-1,3,5-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenylalkyl phosphites, phenyldialkyl phosphites, tris(nonylphenyl) phosphite, trilauryl phosphite, trioctadecyl phosphite, distearylpentaerythritol diphosphite, tris(2,4-di-tert-butylphenyl) phosphite, diisodecyl pentaerythritol diphosphite, bis(2,4-di-tert-butylphenyl)pentaerythritol diphosphite, bis(2,4-dicumylphenyl)pentaerythritol diphosphite, bis(2,6-di-tert-butyl-4-methylphenyl)pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, bis(2,4-di-tert-butyl-6-methylphenyl)methyl phosphite, bis(2,4-di-tert-butyl-6-methylphenyl)ethyl phosphite, 6-fluoro-2,4,8,10-tetra-tertbutyl-12-methyl-dibenz[d,g]-1,3,2-dioxaphosphocin, 2,2',2''-nitrilo[triethyltris(3,3',5,5'-tetra-tertbutyl-1,1'-biphenyl-2,2'-diyl)phosphite], 2-ethylhexyl(3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane, phosphorous acid, mixed 2,4-bis(1,1-dimethylpropyl)phenyl and 4-(1,1-dimethylpropyl)phenyl triesters (CAS: 939402-02-5), phosphorous acid, triphenyl ester, polymer with α-hydro-w-hydroxypoly[oxy(methyl-1,2-ethanediyl)], $C_{10-16}$-alkyl esters (CAS: 1227937-46-3).

The following phosphites are especially preferred:

Tris(2,4-di-tert-butylphenyl) phosphite (Irgafos®168, BASF SE), tris(nonylphenyl) phosphite, bis(2,4-dicumylphenyl)pentaerythritol diphosphite, (A)

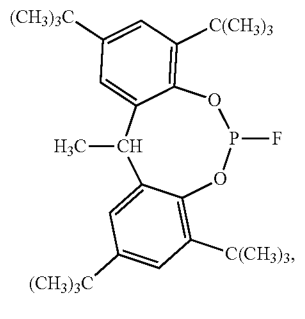

(B)

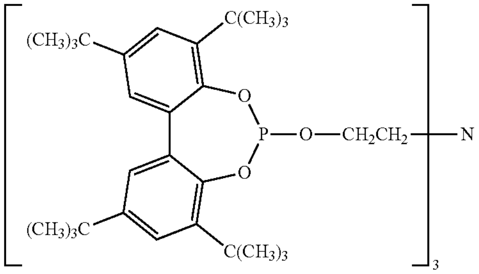

-continued (C)

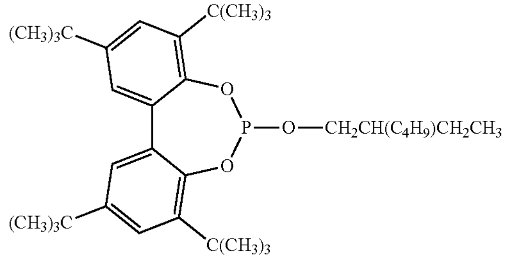

(D)

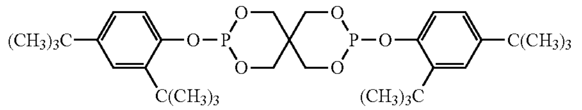

(E)

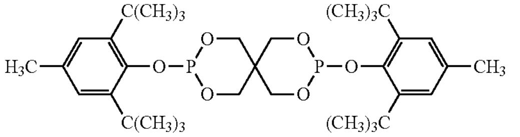

(F)

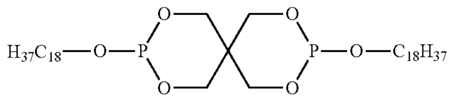

(G)

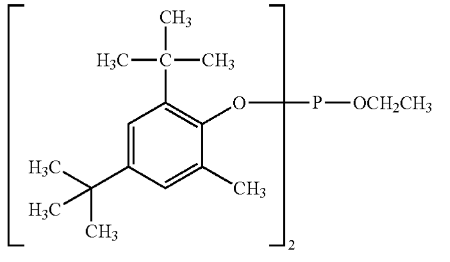

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.
6. Nitrones, for example, N-benzyl-alpha-phenylnitrone, N-ethyl-alpha-methylnitrone, N-octyl-alpha-heptylnitrone, N-lauryl-alpha-undecylnitrone, N-tetradecyl-alpha-tridecylnnitrone, N-hexadecyl-alpha-pentadecylnitrone, N-octadecyl-alpha-heptadecylnitrone, N-hexadecyl-alpha-heptadecylnitrone, N-ocatadecyl-alpha-pentadecylnitrone, N-heptadecyl-alpha-heptadecylnitrone, N-octadecyl-alpha-hexadecylnitrone, nitrone derived from N,N-dialkylhydroxylamine derived from hydrogenated tallow amine.
7. Thiosynergists, for example dilauryl thiodipropionate, dimistryl thiodipropionate, distearyl thiodipropionate or distearyl disulfide.
8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.
9. Polyamide stabilizers, for example copper salts in combination with iodides and/or phosphorus compounds and salts of divalent manganese.
10. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate or zinc pyrocatecholate.
11. Nucleating agents, for example inorganic substances, such as talcum, metal oxides, such as titanium dioxide or magnesium oxide, phosphates including phosphate salts such as 2,2'-methylene-bis(4,6-di-tert-butylphenol) phosphate sodium salt, 2,2'-methylene-bis(4,6-di-tert-butylphenol) phosphate aluminium salt or 2,2'-methylene-bis(4,6-di-tert-butylphenol) phosphate lithium salt, carbonates or sulfates of, preferably, alkaline earth metals; organic compounds, such as mono- or polycarboxylic acids and the salts thereof, e.g. 4-tert-butylbenzoic acid, adipic acid, diphenylacetic acid, sodium succinate or sodium benzoate, 1,2-cyclohexane dicarboxylic acid calcium salt, bicyclo[2.2.1]heptane-2,3-dicarboxylic acid disodium salt; polymeric compounds, such as ionic copolymers (ionomers), triamino benzene derivatives, zinc glycerolate and nonytol derivatives. Especially preferred are 1,3:2,4-bis(3',4'-dimethylbenzylidene)sorbitol, 1,3:2,4-di(paramethyldibenzylidene)sorbitol, and 1,3:2,4-di(benzylidene) sorbitol.
12. Fillers and reinforcing agents, for example calcium carbonate, silicates, surface treated silica (as described e.g. in US-A-2007/60,697 and US-A-2009/111,918), glass fibres, glass beads, asbestos, talc, kaolin, mica, barium sulfate, metal oxides and hydroxides, carbon black, graphite, wood flour and flours or fibers of other natural products, synthetic fibers.
13. Other additives, for example plasticisers, lubricants, emulsifiers, pigments, rheology additives, catalysts, flow-control agents, optical brighteners, flameproofing agents, antistatic agents and blowing agents.
14. Benzofuranones and indolinones, for example those disclosed in U.S. Pat. Nos. 4,325,863; 4,338,244; 5,175,312; 5,216,052; 5,252,643; DE-A-4316611; DE-A-4316622; DE-A-4316876; EP-A-0589839, EP-A-0591102; EP-A-1291384 or 3-[4-(2-acetoxyethoxy) phenyl]-5,7-di-tert-butylbenzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy] phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butylbenzofuran-2-one, 3-(3,5-dimethyl-4-pivaloyloxyphenyl)-5,7-di-tert-butylbenzofuran-2-one, 3-(3,4-dimethylphenyl)-5,7-di-tert-butylbenzofuran-2-one, 3-(2,3-dimethylphenyl)-5,7-di-tert-butylbenzofuran-2-one, 3-(2-acetyl-5-isooctylphenyl)-5-isooctylbenzofuran-2-one, 5,7-ditert-butyl-3-[3,5-dimethyl-4-[(1,3,7,9-tetratert-butyl-5-methyl-5H-benzo[d][1,3,2]benzodioxaphosphocin-11-yl)oxy]phenyl]-3H-benzofuran-2-one.

Preference is given to compositions which additionally contain a further additive selected from the group consisting of antioxidants, processing stabilisers, light stabilisers, UV absorbers, fillers, reinforcing agents, pigments, metal deactivators, plasticisers, lubricants, emulsifiers, rheology additives, catalysts, flow-control agents, optical brighteners, flameproofing agents, antistatic agents and blowing agents.

The weight ratio of the total amount of the compounds of formulae (1) to (3) to the total amount of the conventional additive(s) can be for example 100:1 to 1:1000 or 10:1 to 1:100 or 20 to 1 to 1 to 20 or 10:1 to 1:10.

According to one embodiment, the compositions of the present invention can comprise as a further free radical source a peroxide. In such case a ratio of the sum of the weight of peroxide to the total amount of the weight of compounds of formulae (1) and (2) of 1:100 to 100:1, especially 1:10 to 10:1, is preferred.

Typical peroxides are 2,5-dimethyl-2,5-bis(tert.-butyl-peroxy)hexane (DHBP, for instance sold under the tradenames Luperox 101 and Trigonox 101),

- 2,5-dimethyl-2,5-bis(tert.-butyl-peroxy)hexyne-3 (DYBP, for instance sold under the tradenames Luperox 130 and Trigonox 145),
- dicumyl-peroxide (DCUP, for instance sold under the tradenames Luperox DC and Perkadox BC),
- di-tert.-butyl-peroxide (DTBP, for instance sold under the tradenames Trigonox B and Luperox Di),
- tert.-butyl-cumyl-peroxide (BCUP, for instance sold under the tradenames Trigonox T and Luperox 801),
- bis (tert.-butylperoxyisopropyl)benzene (DIPP, for instance sold under the tradenames Perkadox 14S and Luperox DC),
- 3,6,9-triethyl-3,6,9-trimethyl-1,4,7-triperoxonane (for instance sold under the tradename Trigonox 301),
- di(tert-butylperoxyisopropyl)benzene (for instance sold under the tradename Perkadox 14S-FL), dicetyl peroxydicarbonate (for instance sold under the tradename Perkadox 24L) and tert-butyl monoperoxymaleate (for instance sold under the tradename Perkadox PF-DBM25).

Preferred peroxides are 2,5-dimethyl-2,5-bis(tert.-butyl-peroxy)hexane (DHBP), tert.-butylcumylperoxide (BCUP) and 3,6,9-triethyl-3,6,9-trimethyl-1,4,7-triperoxonane, especially 2,5-dimethyl-2,5-bis(tert.-butyl-peroxy)hexane (DHBP) and 3,6,9-triethyl-3,6,9-trimethyl-1,4,7-triperoxonane.

The compounds of the present composition can be added to the polymeric substrate in the form of a liquid, a powder, granule or a masterbatch, which contain each of the compounds of the present invention in, for example, a concentration of from 0.01 to 90%, preferably 0.05 to 25%, and more preferably by 0.05 to 20%, especially 0.1 to 10% by weight.

The compounds of the present composition and optionally further additives may be added to the polymeric substrate either individually or mixed with one another.

It is preferred that components (a) and (b) are added together, preferably in the form of a masterbatch.

The compounds of the present composition and optionally further additives can be added to a polymer before, during or after the polymerization or before or after the crosslinking.

Compounds of the composition according to the present invention and optionally further additives can be incorporated into the polymeric substrate by known methods, for example before or during shaping or by applying the dissolved or dispersed respective compound to the polymeric substrate, if necessary with subsequent evaporation of the solvent.

The addition of the compounds of the present composition including any further additives, like those given above, to the polymeric substrate can be carried out in all customary mixing machines in which the polymer is melted and mixed with the compounds of the present composition and optionally further additives. Suitable machines are known to those skilled in the art. These are mixers, kneaders and extruders. The process is preferably carried out by adding the compounds of the present composition and optionally further additives during processing in an extruder. Particularly preferred processing machines are single-screw extruders, corotating and counterrotating twin-screw extruders, planetary gear extruders, ring extruders or cokneaders provided with at least one gas removal compartment to which a vacuum can be applied.

The polymers are subjected to an elevated temperature for a sufficient period of time for the molecular weight modification. In a preferred embodiment of the process of the present invention, a temperature range from about 160° C. to 310° C. is employed. In a particularly preferred process variant, the temperature range from about 170° C. to 290° C., in particular about 180-270° C., is used.

The period of time necessary for modifying the molecular weight can vary as a function of temperature, the amount of material to be modified and the type of any extruder employed. It may range, for example, from about 10 seconds to 20 minutes, in particular from 20 seconds to 10 minutes.

Examples of processing or transformation of the compositions according to the present invention are:

Injection blow molding, extrusion, blow molding, rotomolding, in mold decoration (back injection), slush molding, injection molding, co-injection molding, forming, compression molding, pressing, film extrusion (cast film; blown film), fiber spinning, other fiber processing (woven, nonwoven, especially fiber melt blown, spun bonded), drawing (uniaxial, biaxial), annealing, deep drawing, calandering, mechanical transformation, sintering, coextrusion, coating, lamination, crosslinking (radiation, peroxide, silane), vapor deposition, weld together, glue, thermoforming, pipe extrusion, profile extrusion, sheet extrusion; sheet casting, spin coating, strapping, foaming, recycling/rework, extrusion coating.

The materials processed according to this invention can be used in a wide variety of forms, for example as films, fibres (continuous or non-continuous), tapes, or moulded articles.

Fibers, including bicomponent fibers, are preferred.

Bicomponent fibers are meant to be fibers comprising at least two distinct polymeric domains a) and b) in intimate adherence along the length of the fibers. These can be of any shape, and are not limited to a particular shape. Examples of such shapes are side-by-side; sheath-core, orange, and matrix and fibrils types, which are illustrated in Fahrbach, E., Schaut, G. and Weghmann, A., 2000, Nonwoven Fabrics, FIG. 3, Ullmann's Encyclopedia of Industrial Chemistry. Preferred are sheath-core type bicomponent fibers and side-by-side type bicomponent fibers, especially sheath-core type bicomponent fibers.

Preferred articles are nonwoven fabrics which shall also include webs and shall mean a textile structure of individual fibers, filaments, or threads that are directionally or randomly oriented and bonded by friction, and/or cohesion and/or adhesion and/or mechanical process, as opposed to a regular pattern of mechanically inter-engaged fibers, i.e., it is not a woven or knitted fabric. Examples of nonwoven fabrics include meltblown filaments, spunbond continuous filament webs, carded webs, air-laid webs, and wet-laid webs. Suitable bonding methods include thermal bonding, chemical or solvent bonding, resin bonding, mechanical needling, hydraulic needling, stitch-bonding, etc. An overview thereof is given in Fahrbach, E., Schaut, G. and Weghmann, A., 2000, Nonwoven Fabrics, Ullmann's Encyclopedia of Industrial Chemistry. Such nonwovens can for example be prepared from fibers made by use of the inventive compositions. The nonwoven fabrics are especially prepared by use of the inventive fibers.

The inventive composition allows to more efficiently modify the polymeric substrates by change of rheology (vis-breaking, long chain branching, crosslinking).

This allows to improve

- mechanical properties, like tensile strength, elongation, tear resistance
- barrier properties, especially in nonwovens (e.g. hydrohead, air permeability, filter properties)
- processing properties (broader scope of suitable polymers, parameter adaptation, like thermobonding temperature in nonwovens)
- recycling, because the adjustment of the melt viscosity of the recycled polymers can provide a recycled item with more homogeneous molecular weight (narrower MWD) and therefore better mechanical properties. In addition, the use of a vis broken polymer can serve as processing aid or compatibilizer that also contributes to higher mechanical properties of recycled polymers In addition, as the rheological quality of the recycled polymers is variable, the present invention enables to regulate the rheological response of the polymer so that one can have a more steady and controllable process.

Improved properties with respect to tensile strength and elongation are of importance for, for example, the manufacture of nonwoven fabrics, since their preparation involves multiple steps and improved tensile strength or elongation helps to let them better survive these steps.

Importantly, higher tensile strength provides the producer of nonwoven fabrics with the option to e.g. reduce weight while keeping still good mechanical performance of the product.

A further important aspect is the processing safety in the course of the preparation of non-wovens. It is desired to run the process for the preparation of nonwoven fabrics under more moderate conditions at lower process temperature. In order to be able to do so, still good mechanical properties, like tensile strength and elongation, must be obtained at lower process temperature. This allows to reduce the process temperature. Furthermore, energy savings will be a secondary benefit.

A further embodiment of the present invention is directed to a composition comprising a compound of formula (1) or (2) together with a compound of formula (3), for which the above definitions and preferences shall apply.

Another embodiment of the present invention is directed to the use of such composition comprising a compound of formula (1) or (2) together with a compound of formula (3) for modifying the rheology of polymeric substrates. As to such embodiment the above definitions and preferences shall apply.

Furthermore, another embodiment of the present invention is directed to novel compounds of formula (3), as given below:

(13)

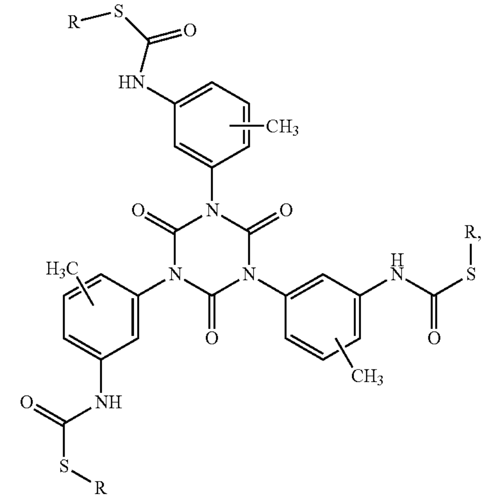

(14)

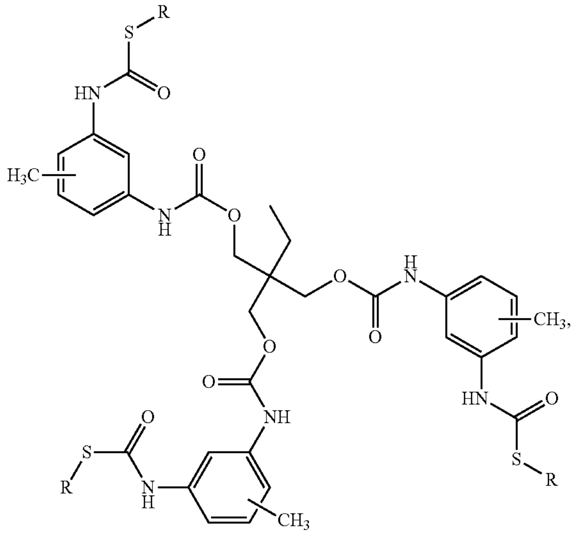

wherein in each of formulae (11) and (12) R is as defined above and for which the above preferences shall apply, or (15)

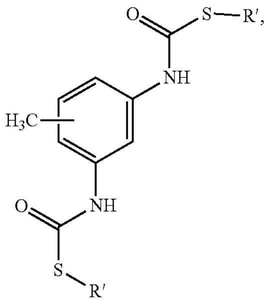

wherein R' is $C_8$-$C_{40}$alkyl which is uninterrupted or interrupted by —O— and/or a carbonyl group, and for which the above preferences given for R shall apply.

Preferred are compounds of formulae (13) and (14), especially those of formula (14).

The following examples illustrate the invention in greater detail. All percentages and parts are by weight, unless stated otherwise.

EXAMPLES

Synthesis Example 1

(101)

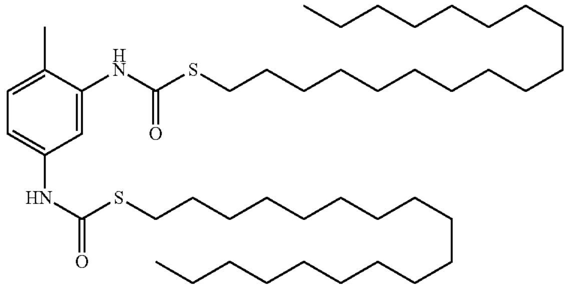

In 250 ml of anhydrous tetrahydrofurane are dissolved 17.4 g (0.1 mol) toluene-2,4-diisocyanate and 60.18 g (0.21 mol) of 1-octadecanethiol. To the stirred solution is added 1 g of 1,8-diazabicyclo[5,4,0]undec-7-ene. The stirring is continued for 1 hour at room temperature. The white suspension is then evaporated to dryness on a rotary evaporator, and the residue is recrystallized from ethyl acetate to afford 67.7 g of the title compound as a white solid, melting point 103-103.5° C.

Synthesis Example 2

(102)

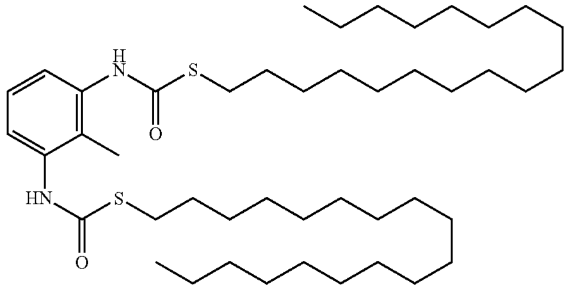

Repeating Synthesis Example 1, but replacing therein toluene-2,4-diisocyanate by an equimolar amount of toluene-2,6-diisocyanate, results in the compound of formula (102), obtained as a white solid, melting point 120-122° C.

Synthesis Example 3

Isomer mixture comprising 80 weight-% of the compound of formula (103)

(103)

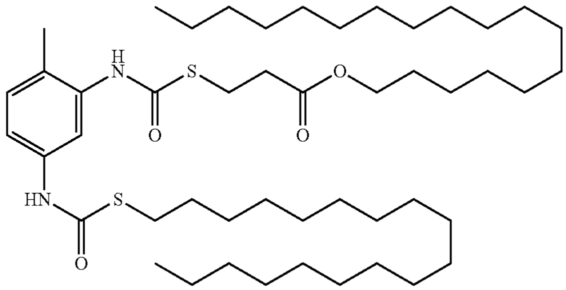

and 20 weight-% of the compound of formula (104)

(104)

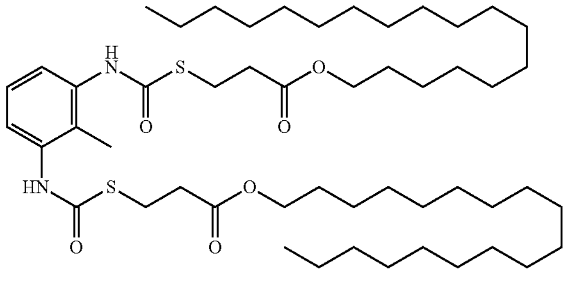

Repeating Synthesis Example 1, but replacing therein toluene-2,4-diisocyanate by an equimolar amount of an isomer mixture of toluene-2,4-diisocyanate/toluene-2,6-diisocyanate in a weight ratio of 80/20, and replacing octadecanethiol by an equimolar amount of octadecyl-3-mercaptopropionate, results in the isomer mixture of the compounds of formulae (103) and (104) in a weight ratio of 80/20, obtained as a white solid, melting point 94-100° C.

Synthesis Example 4

Reaction mixture comprising the compound of formula (105) as one main component (105)

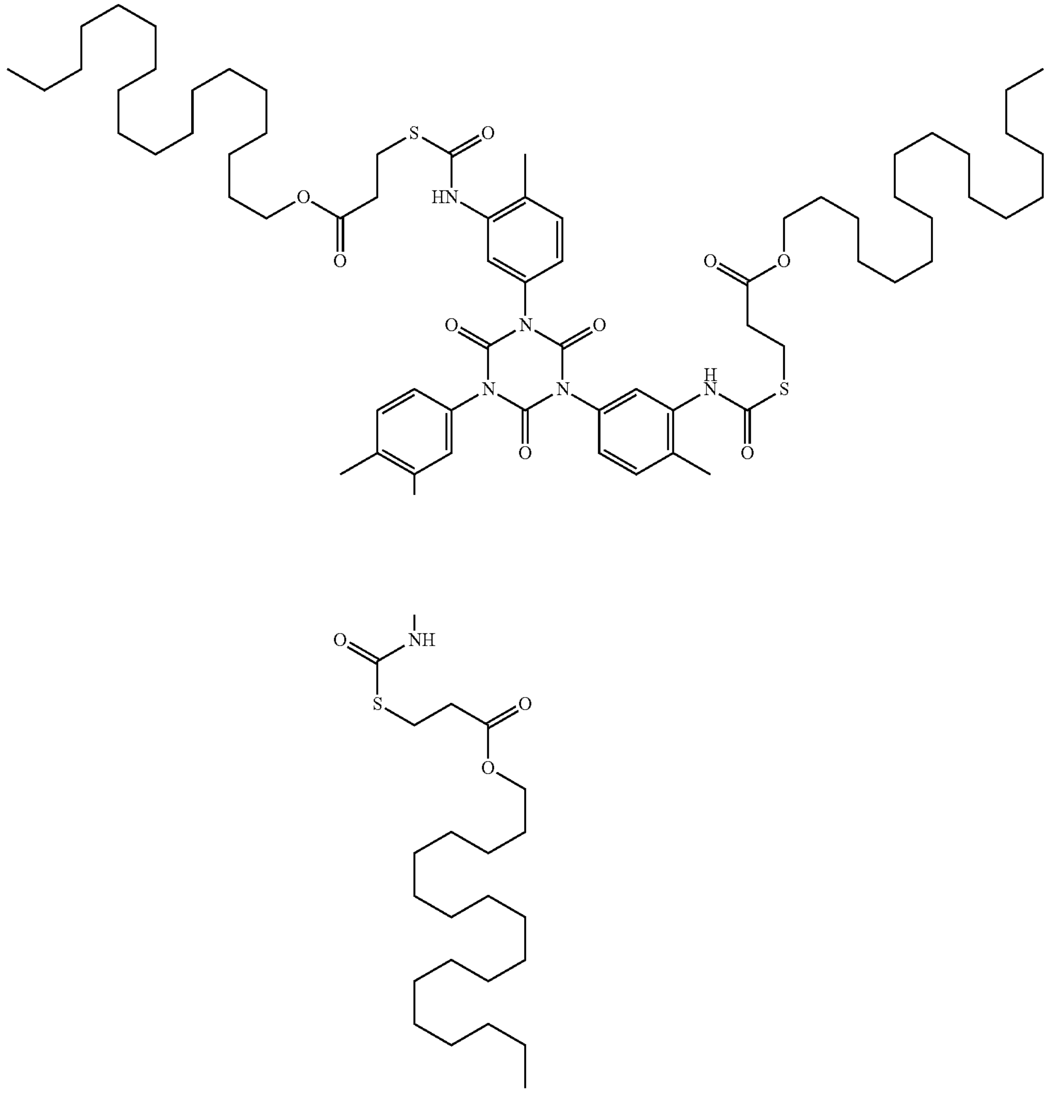

63.26 g octadecyl-3-mercaptopropionate and 5 ml triethylamine are dissolved in 400 ml ethyl acetate under argon. Then, 100 g of Desmodur® IL EA (50% in ethyl acetate, available from Covestro AG) are diluted with 100 ml ethyl acetate and added to the above solution which is then stirred for one hour at 50° C. After 90 minutes, no octadecyl-3-mercaptopropionate is detectable by $^1$H-NMR in $CDCl_3$. The mixture is then filtered and the filtrate is evaporated (20 mbar/50° C.). The obtained solid is grinded and then dried during 1.5 hours at 0.45 mbar/50° C. and then for 114 hours at 50° C./200 mbar to afford 110.8 g of a beige solid which comprises the compound of formula (105) as one main component.

Synthesis Example 5

Reaction mixture comprising the compound of formula (106) as one main component (108)
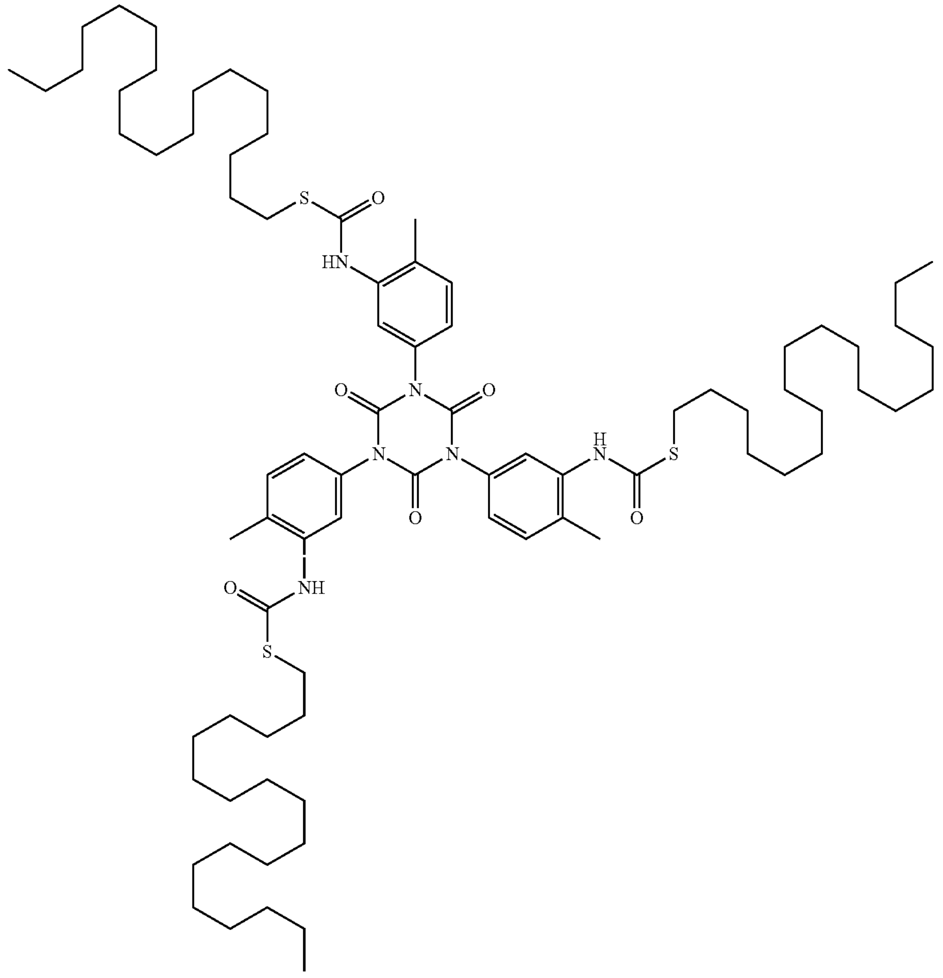
Repeating Synthesis Example 4, but replacing therein octadecyl-3-mercaptopropionate by an equimolar amount of octadecanethiol, results in a mixture comprising the compound of formula (106) as one main component.
Synthesis Example 6
Mixture comprising the compound of formula (107) as one main component (107)

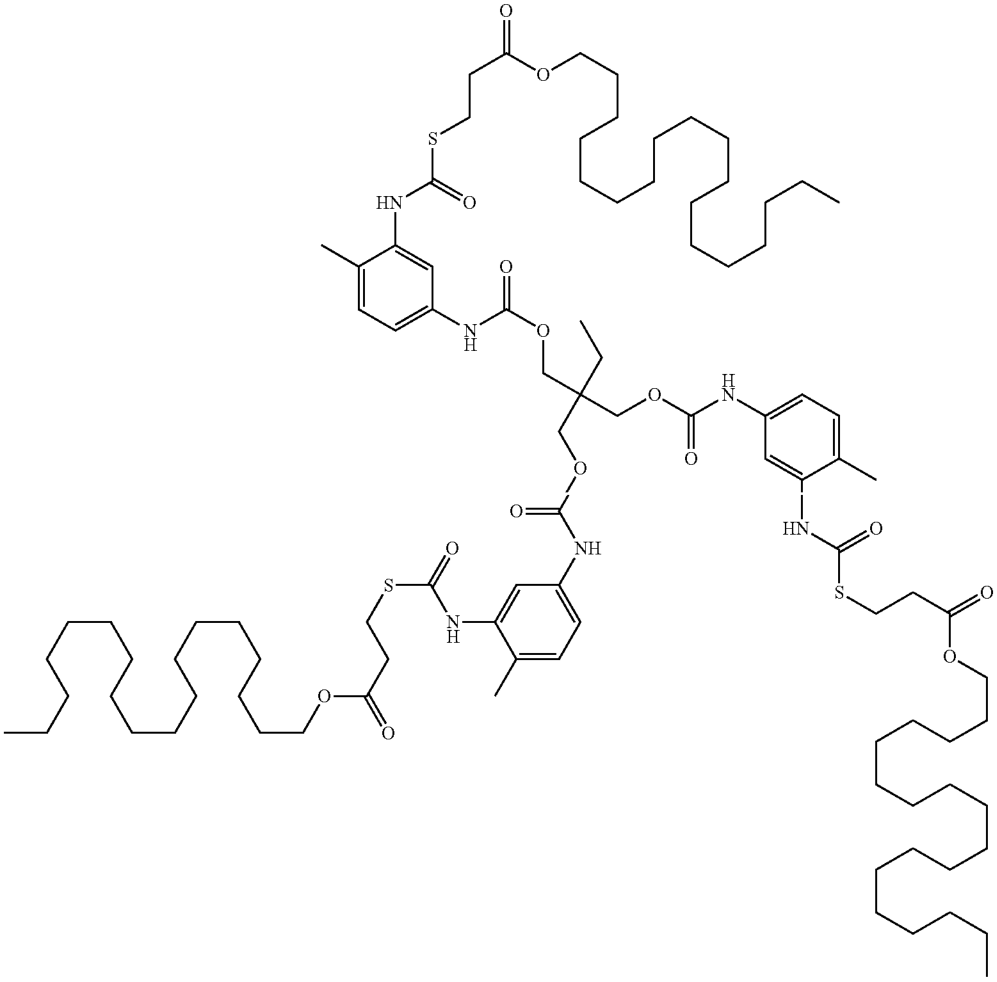

102.21 g octadecyl-3-mercaptopropionate and 5 ml triethylamine are dissolved in 400 ml ethyl acetate under argon. Then, 100 g of Desmodur® L75 (75% in ethyl acetate, available from Covestro AG) are dissolved in 100 ml ethyl acetate and added to the above solution which is then stirred for one hour at 50° C. After 90 minutes, no octadecyl-3-mercaptopropionate is detectable by $^1$H-NMR in $CDCl_3$. The mixture is then evaporated on a rotary evaporator, at the end at 0.05 mbar/50° C. The obtained waxy product is additionally dried at 50° C./200 mbar until constant weight to afford 167.71 g of a beige solid which comprises the compound of formula (107) as one main component.

(108)

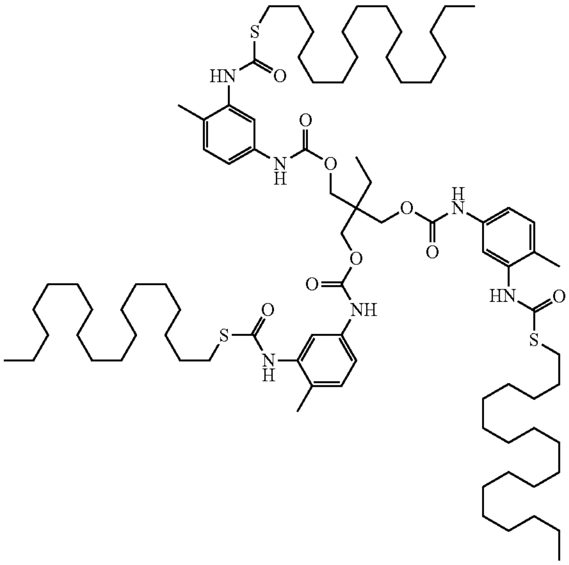

Synthesis Example 7

Mixture comprising the compound of formula (108) as one main component

Repeating Synthesis Example 6, but replacing therein octadecyl-3-mercaptopropionate by an equimolar amount of octadecanethiol, results in a mixture comprising the compound of formula (108) as one main component.

A) Application Examples—Meltblown Nonwovens

Application Examples A1 to A31

Meltblown nonwovens are produced on a MB-L 150/200 equipment from RAVOtec GmbH. The feeding extruder is a single-screw extruder with screw diameter 25 mm, length to diameter ratio 25 and with four heating zones. Unless otherwise stated, the screw rotational speed is 50 rotations per minute. As reference temperature, the melt temperature at the end of the extruder is recorded and listed in the below examples. The meltblown equipment has a nozzle with 35 holes per square inch, each hole having a diameter of 0.35 mm. Unless otherwise stated, the air volume is 360 $m^3$/hour. The distance from the conveyor to the die is 250 mm. The die has a width of 200 mm. The grammage of the nonwovens is 20 g/$m^2$, unless otherwise stated.

The polymer used for the tests is a polypropylene homopolymer with melt flow index of 25.0 g/10 min (230° C., 2.16 kg) and density of 0.9 g/$cm^3$. It is a grade stabilized with 0.05% of phenolic antioxidant, 0.1% of phosphite and 0.025% wt. of calcium stearate.

The melt flow rate is measured according to ISO 1133 (230° C., 2.16 kg). The measurements are carried out on the nonwovens which are cut into fine pieces. The melt flow rate is a crucial parameter for the meltblown process. A sufficiently high melt flow rate is necessary to enable the production of nonwovens of good quality. The hydrostatic head (water column) and the air permeability are applicative parameters that serve to define the quality of the produced nonwovens.

The hydrostatic head measures the pressure required to force drops of water through the tautly held fabric. It is a measure of the resistance of nonwoven fabrics to the penetration of water. The measurement is performed in accordance with WSP (World Strategic Partner) 80.6 (2005). The test is performed with a test head of 100 $cm^2$ at a water pressure increase rate of 10±0.5 cm $H_2O$/min. The result is given as the water column height—or hydrostatic head, or hydrohead—in mm, when the third drop protrudes though the nonwoven.

The air permeability is measured according to WSP (World Strategic Partner) 70.1 (2005). The pressure difference is 200 Pa and the sample size 20 $cm^2$. The result is given in l/$m^2$/s, so it defines the volume of air flowing perpendicularly through a section of nonwoven of surface of 1 $m^2$ per second.

Unless otherwise stated, the given percentages are in % wt.

The product named NOR1 hereafter corresponds to the compound of formula (5)

(5)

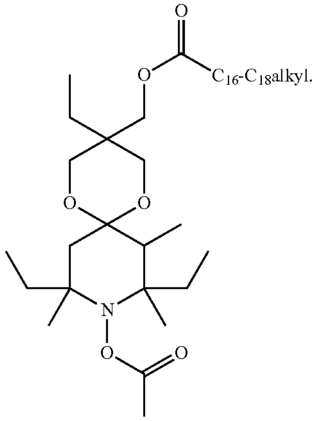

Unless otherwise stated, the products are firstly incorporated into a homo polypropylene with melt flow index of 25.0 g/10 min (230° C., 2.16 kg) and density of 0.9 g/$cm^3$ at a concentration in weight-% given in the below tables, with a co-rotating twin screw extruder with screw diameter of 25 mm and ratio length to diameter of 42, at a melt temperature of 210° C. So such pre-mixtures can be considered as masterbatches. For all masterbatches, every product present in the second column of below Tables 1 to 3 is each incorporated in a separate masterbatch (resulting in two different masterbatches), except for below Examples A30 and A31, where both products were incorporated into the same masterbatch (combibatch). The concentration of the product in the corresponding masterbatch is shown in the third column of below Tables 1 to 3.

TABLE 1

(processing at 295° C.)

| Ex. | Recipe (concentration in tested polymer) | Concentration in masterbatch [weight-%] | Hydrostatic head at $3^{rd}$ drop [mm] | Air permeability at 20 $cm^2$, 200 Pa [l/$m^2$/s] | MFR at 230° C., 2.16 kg [g/10 min] |
|---|---|---|---|---|---|
| A1 | 400 ppm NOR1 | 3.3 | 502 | 998 | 1095 |
| A2 | 350 ppm NOR1 + 50 ppm product of Synthesis Ex. 1 | 3.3 + 3.3 | 651.2 | 653 | 1149.3 |
| A3 | 300 ppm NOR1 + 100 ppm product of Synthesis Ex. 1 | 3.3 + 3.3 | 593 | 411 | 1639.8 |
| A4 | 400 ppm NOR1 + 100 ppm product of Synthesis Ex. 5 | 3.3 + 1 | 594 | 460 | 1524.6 |

TABLE 1-continued (processing at 295° C.)

| Ex. | Recipe (concentration in tested polymer) | Concentration in masterbatch [weight-%] | Hydrostatic head at $3^{rd}$ drop [mm] | Air permeability at 20 $cm^2$, 200 Pa [I/$m^2$/s] | MFR at 230° C., 2.16 kg [g/10 min] |
|---|---|---|---|---|---|
| A5 | 300 ppm NOR1 + 100 ppm product of Synthesis Ex. 3 | 3.3 + 3.3 | 778.6 | 478.4 | 1652.3 |
| A6 | 267 ppm NOR1 + 67 ppm product of Synthesis Ex. 3 | 3.3 + 3.3 | 607 | 811.6 | 1308.2 |
| A7 | 300 ppm NOR1 + 100 ppm product of Synthesis Ex. 6 | 3.3 + 3.3 | 678 | 753.6 | 1270.4 |
| A8 | 400 ppm NOR1 + 100 ppm product of Synthesis Ex. 4 | 3.3 + 3.3 | 756.4 | 643.6 | 1458.1 |

The results in Table 1 exhibit the superior quality of the nonwoven, either in terms of water column, air permeability or melt flow rate.

TABLE 2

(processing at 270° C.)

| Ex. | Recipe (concentration in tested polymer) | Loading in masterbatch [weight-%] | Hydrostatic head at $3^{rd}$ drop [mm] | Air permeability at 20 $cm^2$, 200 Pa [I/$m^2$/s] | MFR at 230° C., 2.16 kg [g/10 min] |
|---|---|---|---|---|---|
| A9 | 400 ppm NOR1 | 3.3 | 187 | 2668.0 | 651.2 |
| A10 | 350 ppm NOR1 + 50 ppm product of Synthesis Ex. 1 | 3.3 + 3.3 | 570.0 | 897 | 931.3 |
| A11 | 300 ppm NOR1 + 100 ppm product of Synthesis Ex. 1 | 3.3 + 3.3 | 706.6 | 554 | 1217.8 |
| A12 | 350 ppm NOR1 + 50 ppm product of Synthesis Ex. 5 | 3.3 + 1 | 201 | 2618 | 724.8 |
| A13 | 300 ppm NOR1 + 100 ppm product of Synthesis Ex. 5 | 3.3 + 1 | 275 | 2192 | 895.8 |
| A14 | 400 ppm NOR1 + 100 ppm product of Synthesis Ex. 5 | 3.3 + 1 | 377 | 1396 | 1062.9 |
| A15 | 300 ppm NOR1 + 100 ppm product of Synthesis Ex. 3 | 3.3 + 3.3 | 470.6 | 1082.0 | 1094.9 |
| A16 | 267 ppm NOR1 + 67 ppm product of Synthesis Ex. 3 | 3.3 + 3.3 | 471.2 | 1472.0 | 1365.3 |
| A17 | 300 ppm NOR1 + 100 ppm product of Synthesis Ex. 6 | 3.3 + 3.3 | 203.5 | 2752.5 | 685.7 |

TABLE 2-continued (processing at 270° C.)

| Ex. | Recipe (concentration in tested polymer) | Loading in masterbatch [weight-%] | Hydrostatic head at $3^{rd}$ drop [mm] | Air permeability at 20 $cm^2$, 200 Pa [I/$m^2$/s] | MFR at 230° C., 2.16 kg [g/10 min] |
|---|---|---|---|---|---|
| A18 | 400 ppm NOR1 + 100 ppm product of Synthesis Ex. 6 | 3.3 + 3.3 | 510.6 | 1084.0 | 1201.3 |
| A19 | 267 ppm NOR1 + 133 ppm product of Synthesis Ex. 6 | 3.3 + 3.3 | 304.6 | 2206.0 | 1006.1 |
| A20 | 400 ppm NOR1 + 100 ppm product of Synthesis Ex. 4 | 3.3 + 3.3 | 237.4 | 2432.5 | 863.3 |

The results in Table 2 exhibit the superior quality of the nonwoven, either in terms of water column, air permeability or melt flow rate.

TABLE 3

(processing at 250° C.)

| Ex. | Recipe (concentration in tested polymer) | Loading in masterbatch [weight-%] | Hydrostatic head at $3^{rd}$ drop [mm] | Air permeability at 20 $cm^2$, 200 Pa [I/$m^2$/s] | MFR at 230° C., 2.16 kg [g/10 min] |
|---|---|---|---|---|---|
| A21 | 400 ppm NOR1 | 3.3 | 174.25 | 3360 | 509.9 |
| A22 | 350 ppm NOR1 + 50 ppm product of Synthesis Ex. 1 | 3.3 + 3.3 | 310.6 | 1814 | 908.9 |
| A23 | 300 ppm NOR1 + 100 ppm product of Synthesis Ex. 1 | 3.3 + 3.3 | 269.0 | 2108 | 955.3 |
| A24 | 400 ppm NOR1 + 100 ppm product of Synthesis Ex. 1 | 3.3 + 3.3 | 484.2 | 1368.0 | 1265.5 |
| A25 | 400 ppm NOR1 + 100 ppm product of Synthesis Ex. 5 | 3.3 + 1 | 152 | 2770 | 808.9 |
| A26 | 300 ppm NOR1 + 100 ppm product of Synthesis Ex. 3 | 3.3 + 3.3 | 243.2 | 2034.0 | 601.7 |
| A27 | 400 ppm NOR1 + 100 ppm product of Synthesis Ex. 3 | 3.3 + 3.3 | 250.4 | 2232.0 | 1198.3 |
| A28 | 300 ppm NOR1 + 100 ppm product of Synthesis Ex. 6 | 3.3 + 3.3 | 162.8 | 3286 | 645.6 |
| A29 | 400 ppm NOR1 + 100 ppm product of Synthesis Ex. 6 | 3.3 + 3.3 | 347.2 | 1982.0 | 853.6 |
| A30 | 300 ppm NOR1 + 100 ppm product of Synthesis Ex. 6 | 3.3 + 0.825 Combibatch | 332.6 | 1918.0 | 1084.7 |
| A31 | 400 ppm NOR1 + 100 ppm product of Synthesis Ex. 6 | 3.3 + 0.825 Combibatch | 601.0 | 1042.0 | 1627.4 |

The results of Table 3 exhibit the superior quality of the nonwoven, either in terms of water column, air permeability or melt flow rate. The results also show that the incorporation of both products into the same masterbatch (combi-batch), instead of using two separate masterbatches, can provide an even higher vis-breaking performance.

B) Application Examples—Extrusion

Application Examples B1 to B15

The performance of the various products is determined in a reproducible and systemic way by using a lab scale twin-screw mini-extruder. The polymer used is a polypropylene homopolymer with melt flow index of 3.0 g/10 min (230° C., 2.16 kg) and density of 0.9 g/cm$^3$. It is a non-stabilized grade, in which 0.1% wt. Irganox® B215 (commercial stabilizing blend consisting of Irgafos®168+Irganox®1010) and 0.05% wt. of calcium stearate are added. Calcium stearate is used in powder form, without a pre-drying step. Unless otherwise stated, the additives indicated in the tables below are mixed to the polypropylene powder and the mixture is compounded in a lab scale twin-screw mini-extruder (Xplore Instruments B.V.) with co-rotating screws and volume of 15 cm$^3$ in a loop system during ten minutes at constant screw rotating speed (indicated in the below examples) under nitrogen blanket. The percentages given below are weight percent. The melt temperature is given in the below examples. The lab scale twin-screw mini-extruder records the backpressure force in real time, at a rate of one measurement per second. Upon filling the barrel, the force rises to a maximum, before starting to decrease. This force maximum is taken as time zero. For the comparison of the contribution of the various products, the force after 600 seconds after time zero is taken into account. The reference recipe, always indicated in the below tables, corresponds to a force reduction of 0%. If one achieves a compounding force of 0 Newton at 600 seconds, then the force reduction would be 100%.

The recorded force directly correlates with the melt viscosity of the polymer. So the lower the molecular weight of the polymer, the lower its melt viscosity, and the lower the recorded force. Therefore, the recorded force is a direct measure of the melt flow of the polymer.

For the fabrication of nonwovens, for instance in spunbond or meltblown processes, having a melt flow high enough is decisive, firstly to be able to process the polypropylene, and secondly to obtain nonwovens with a satisfactory quality.

For the tests in Table 4, the reference in addition always comprises 0.15% of the compound of formula (5). The extrusion temperature is 270° C., with a screw rotational speed of 50 rotations per minute.

TABLE 4

| Ex. | Recipe (concentration in tested polymer) | Reduction in compounding force after 600 seconds, beyond the reference recipe |
|---|---|---|
| B1 | Reference | 0 |
| B2 | Reference + 39 ppm product of Synthesis Ex. 3 | 33.7 |
| B3 | Reference + 44 ppm product of Synthesis Ex. 7 | 30.5 |
| B4 | Reference + 50 ppm product of Synthesis Ex. 6 | 39.1 |
| B5 | Reference + 33 ppm product of Synthesis Ex. 2 | 38.8 |
| B6 | Reference + 33 ppm product of Synthesis Ex. 1 | 42.0 |
| B7 | Reference + 40 ppm product of Synthesis Ex. 5 | 21.0 |
| B8 | Reference + 47 ppm product of Synthesis Ex. 4 | 26.3 |
| B9 | Reference + 155 ppm product of Synthesis Ex. 3 | 63.9 |
| B10 | Reference + 176 ppm product of Synthesis Ex. 7 | 61.7 |
| B11 | Reference + 200 ppm product of Synthesis Ex. 6 | 59.2 |
| B12 | Reference + 130 ppm product of Synthesis Ex. 2 | 62.2 |
| B13 | Reference + 130 ppm product of Synthesis Ex. 1 | 58.9 |
| B14 | Reference + 161 ppm product of Synthesis Ex. 5 | 46.1 |
| B15 | Reference + 186 ppm product of Synthesis Ex. 4 | 51.1 |

High values are desired.

The results of Table 4 exhibit significantly higher reductions of the compounding force, i.e. lower compounding forces, i.e. higher vis-breaking, when the products of Synthesis 1 to 7 are added.

Application Examples B16 to B20

The tests are carried out as given above for Application Examples B1 to B15, but the co-additives of the Synthetic Examples are not incorporated into the polypropylene directly as such, but are first loaded into a porous polypropylene carrier, at the following concentrations:

For product of Synthetic Example 7 the loading is: 1.855 g product of Synthetic Example 7+100 g polypropylene porous carrier For product of Synthetic Example 6 the loading is: 1.741 g product of Synthetic Example 6+100 g polypropylene porous carrier

TABLE 5

| | Recipe (concentration in tested polymer) | Reduction in compounding force after 600 seconds, beyond the reference recipe |
|---|---|---|
| B16 | Reference | 0 |
| B17 | Reference + 46 ppm product of Synthetic Ex. 7 | 47.2 |
| B18 | Reference + 43 ppm product of Synthetic Ex. 6 | 25.3 |
| B19 | Reference + 184 ppm product of Synthetic Ex. 7 | 55.0 |
| B20 | Reference + 172 ppm product of Synthetic Ex. 6 | 49.9 |

Table 5 shows that, even if the co-additive is not directly incorporated but loaded first in a carrier (porous as exemplified above), the vis-breaking performance remains present.

Application Examples B21 to B23

The tests are carried out as given above for Application Examples B1 to B15, but without the use of the compound of formula (5).

TABLE 6

| | Recipe (concentration in tested polymer) | Reduction in compounding force after 600 seconds, beyond the reference recipe |
|---|---|---|
| B21 | Reference (with 0.15% of the compound of formula (5)) | 0 |
| B22 | 200 ppm of product of Synthetic Example 3 (but without the compound of formula (5)) | 0.8 |
| B23 | 500 ppm of product of Synthetic Example 3 (but without the compound of formula (5)) | 6.3 |

In summary, the Table 6 shows that low performance is obtained if the compound of formula (5) or the co-additives are used alone. In contradistinction thereto, the use of the combination of both components shows a synergistic effect and results in good performance.

C) Application Examples—Nonwovens Produced According to Spunbond Process

Application Examples C1 to C8

Spunbond nonwovens are produced with polypropylene homopolymer with melt flow index of 3.0 g/10 min (230° C., 2.16 kg) and density of 0.9 g/cm$^3$ with and without the additive prepared as given below, on a 1 m wide Reicofil-4 line with a single beam having around 6800 holes per meter length. The holes have a diameter of 0.6 mm. The throughput per hole is set at 0.5 g/min. The line has a sheath-core configuration with a setting of 30% by weight of the polymer in the sheath and 70% by weight of the polymer in the core. The additive-containing fibers comprise the additive in the whole fiber (sheath and core). Nonwovens are produced with a fabric weight of 17 g/m$^2$ (line speed: 212 m/min) and 70 g/m$^2$ (line speed: 53 m/min), respectively. Target filament fineness is 1.7 dtex. Dtex is a unit of measure for the linear mass density of fibers and is defined as the mass in grams per 10000 meters. The nonwovens are thermally bonded using an embossed roll.

The additives are firstly introduced via a masterbatch preparation. The masterbatch is prepared by compounding the product of formula (5), respectively the product of the indicated Synthetic Example, with a polypropylene homopolymer carrier with melt flow index of 25.0 g/10 min (230° C., 2.16 kg), in a co-rotating twin screw extruder with screw diameter of 25 mm and ratio length/diameter of 47, at 200° C. The masterbatches containing the product of formula (5) and the product of the indicated Synthetic Example were two different masterbatches, each containing one product.

Further processing conditions on the Reicofil-4 line are given below:

the extruder temperature is the set temperature used for extrusion of the polypropylene or polypropylene/additive compound and is indicated in the tables;

the die temperature is the set temperature of the polymer on the die;

the cabin pressure is the pressure in the cabin after and below the die;

the engraved and smooth rolls are rolls between which the fiber web is passed;

the nip pressure is the set pressure between the engraved and smooth roll.

Evaluation of Mechanical Properties:

The mechanical properties of the nonwoven fabrics are determined according to DIN EN 29073-3 with a sample clamping length of 100 mm, sample width of 50 mm, advance (deformation speed) of 200 mm/min.

The tensile strength MD and tensile elongation MD are the corresponding maximum values measured in machine direction.

The tensile strength MC and the tensile elongation MC are the corresponding maximum values measured in a direction perpendicular to the machine direction.

TABLE 7

(fabric weight of nonwoven: 70 g/m$^2$)
Set die temperature: 270° C.
Cabin pressure: 4500 Pa
Temperature of engraved roll: 162° C.; smooth roll: 160° C.
Nip pressure: 90 N/mm

| | | Tensile strength MD [N] | Tensile strength MC [N] | Elongation MD [%] | Elongation MC [%] |
|---|---|---|---|---|---|
| C1 | No additive, 295° C. | Not processable—too high pressure | Not processable—too high pressure | Not processable—too high pressure | Not processable—too high pressure |
| C2 | 30 ppm NOR1, in core and in sheath; 295° C. | 234 | 136 | 170.2 | 149.8 |
| C3 | 100 ppm NOR1, in core and in sheath; 280° C. | Not processable—too high pressure | Not processable—too high pressure | Not processable—too high pressure | Not processable—too high pressure |
| C4 | 40 ppm NOR1 + 15 ppm product of Synthesis Ex. 1, both in core and in sheath; 280° C. | 226.6 | 138.9 | 174 | 158.5 |

TABLE 8

(fabric weight of nonwoven: 17 g/m$^2$)
Set die temperature: 270° C.
Cabin pressure: 4500 Pa
Temperature of engraved roll: 162° C.; smooth roll: 160° C.
Nip pressure: 90 N/mm

| | | Tensile strength MD [N] | Tensile strength MC [N] | Elongation MD [%] | Elongation MC [%] |
|---|---|---|---|---|---|
| C5 | No additive 295° C. | Not processable—too high pressure | Not processable—too high pressure | Not processable—too high pressure | Not processable—too high pressure |
| C6 | 30 ppm NOR1, in core and in sheath; 295° C. | 33.7 | 19.5 | 97.4 | 93.3 |
| C7 | 100 ppm NOR1, in core and in sheath; 280° C. | Not processable—too high pressure | Not processable—too high pressure | Not processable—too high pressure | Not processable—too high pressure |

TABLE 8-continued (fabric weight of nonwoven: 17 g/m[2])
Set die temperature: 270° C.
Cabin pressure: 4500 Pa
Temperature of engraved roll: 162° C.; smooth roll: 160° C.
Nip pressure: 90 N/mm

| | | Tensile strength MD [N] | Tensile strength MC [N] | Elongation MD [%] | Elongation MC [%] |
|---|---|---|---|---|---|
| C8 | 40 ppm NOR1 + 15 ppm product of Synthesis Ex. 1, both in core and in sheath; 280° C. | 36 | 19.1 | 110.5 | 87.9 |

The results clearly demonstrate the advantages of the present invention, according to which significantly lower processing temperatures can be used to be able to run a stable process and achieving at least similar mechanical properties, when compared to the use of NOR1 alone as a vis-breaking additive. This, for example, provides the producer of nonwovens with the option to widen his flexibility in polymer choice and sourcing and reducing the processing temperature to save energy while keeping the targeted properties of the nonwoven products.

D) Application Examples—Nonwovens Produced According to Spunbond Process with Improved Thermobonding Behavior

Application Examples D1 to D3

Spunbond nonwovens are produced with polypropylene homopolymer (melt flow index of 27 g/10 min (230° C., 2.16 kg)) with and without the additive prepared as given below, on a 1 m wide Reicofil-4 line with a single beam having around 6800 holes per meter length. The holes have a diameter of 0.6 mm. The throughput per hole is set at 0.55 g/min. The line has a sheath-core configuration with a setting of 30% of the polymer in the sheath and 70% by weight of the polymer in the core. The additive-containing fibers comprise the additive in the sheath layer only. The nonwovens are produced with a fabric weight of 70 g/m[2] (line speed: 53 m/min). The target filament fineness is 1.85 dtex. Dtex is a unit of measure for the linear mass density of fibers and is defined as the mass in grams per 10000 meters. The nonwovens are thermally bonded using an embossed roll.

The additives are firstly introduced via a masterbatch preparation. The masterbatch is prepared by compounding the product of formula (5), respectively the product of the indicated Synthetic Example, with a polypropylene homopolymer carrier with melt flow index of 25.0 g/10 min (230° C., 2.16 kg), in a co-rotating twin screw extruder with screw diameter of 25 mm and ratio length/diameter of 47, at 200° C.

Further processing conditions on the Reicofil-4 line are given below:

the extruder temperature is the set temperature used for extrusion of the polypropylene or polypropylene/additive compound and is indicated in the tables;

the die temperature is the set temperature of the polymer on the die;

the cabin pressure is the pressure in the cabin after and below the die;

the engraved and smooth rolls are rolls between which the fiber web is passed;

the nip pressure is the set pressure between the engraved and smooth roll.

TABLE 9

(fabric weight of nonwoven: 70 g/m[2])
Set extruder and set die temperature: 250° C.
Cabin pressure: 4500 Pa
Temperature of engraved roll: 158° C.; smooth roll: 155° C.
Nip pressure: 80 N/mm

| | | Tensile strength MD [N] | Tensile strength MC [N] | Elongation MD [%] | Elongation MC [%] |
|---|---|---|---|---|---|
| D1 | PP (no additive in sheath) | 147 | 85.2 | 57.9 | 61.5 |
| D2 | 37.5 ppm NOR1 12.5 ppm product of Synthesis Ex. 6, in sheath | 262.2 | 161 | 127.1 | 126.3 |
| D3 | 50 ppm NOR1 | 258.2 | 159.2 | 114.4 | 112.9 |

The results clearly demonstrate the advantages of the present invention, according to which in a thermobonding process significantly better results can be obtained with respect to mechanical properties, when compared to the use of no additive or the use of NOR1 only. This, for example, provides the producer of nonwovens with the option to reduce weight while keeping still good mechanical performance of the product. In addition, when compared to the use of NOR1 only as a vis-breaking additive, this, for example, provides the producer of nonwovens with the option of widening his flexibility in polymer choice and sourcing and reducing the processing temperature to save energy while keeping the targeted properties of the nonwoven products.

The invention claimed is:

1. A composition comprising:

(a) a compound of formula (1) or (2)

(1)

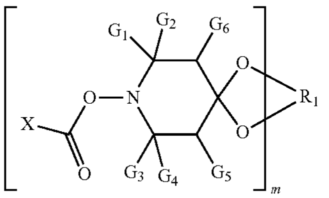

or (2)

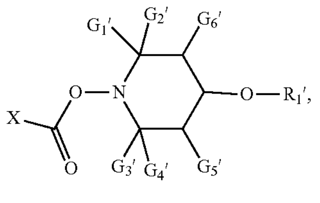

wherein $G_1$, $G_2$, $G_3$ and $G_4$ are each independently of each other $C_1$-$C_4$ alkyl, or $G_1$ and $G_2$ together or $G_3$ and $G_4$ together are pentamethylene;

$G_1'$, $G_2'$, $G_3'$ and $G_4'$ are each independently of each other $C_1$-$C_4$ alkyl, or $G_1'$ and $G_2'$ together or $G_3'$ and $G_4'$ together are pentamethylene;

$G_5$, $G_6$, $G_5'$ and $G_6'$ are each independently of each other hydrogen or $C_1$-$C_4$ alkyl; and X and X' are independently of each other hydrogen, $C_1$-$C_{18}$ alkyl, $C_2$-$C_{18}$ alkenyl, —O—$C_1$-$C_{18}$ alkyl, —NH—$C_1$-$C_{18}$ alkyl, —N($C_1$-$C_6$ alkyl)$_2$, phenyl, phenoxy or —NH-phenyl, m is 1 or 2, and when m is 1, $R_1$ is $C_2$-$C_8$ alkylene, $C_2$-$C_8$ hydroxyalkylene or $C_4$-$C_{36}$ acyloxyalkylene, or when m is 2, $R_1$ is (—$CH_2$)$_2$C($CH_2$—)$_2$, and $R_1$' is hydrogen, $C_1$-$C_8$ alkyl, $C_1$-$C_8$ hydroxyalkyl or a group of formula —(C═O)—$C_1$-$C_{40}$ alkyl, or O—$R_1$' together with a —CH— group linking them are a group —(C═O)—, (b) a compound of formula (3)

(3)

$$A-\!\!\!\!-[S-R]_n,$$

wherein

A is based on an organic isocyanate, wherein radical(s) —S—R are introduced by reaction with isocyanate groups, R is $C_2$-$C_{40}$ alkyl which is optionally substituted and/or interrupted, and n is equal to or greater than 1, and (c) a polymeric substrate.

2. The composition according to claim 1, wherein component (a) is a compound of formula (1).

3. The composition according to claim 2, wherein component (a) is a compound of formula (1), m is 1 and $R_1$ is $C_4$-$C_{36}$ acyloxyalkylene.

4. The composition according to claim 1, wherein component (a) is a compound of formula (5)

(5)

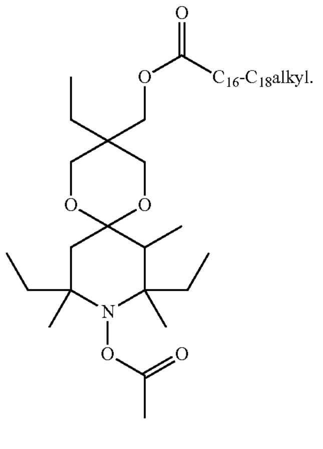

5. The composition according to claim 1, wherein the organic isocyanate is a cyclohexyl diisocyanate, methylenebis(cyclohexyl) diisocyanate, isophorone diisocyanate, phenyl diisocyanate, diphenylmethane diisocyanate or naphthyl diisocyanate, each of which is unsubstituted or substituted by $C_1$-$C_4$ alkyl or di($C_1$-$C_4$ alkyl)amino, or wherein the organic isocyanate is $C_4$-$C_{20}$ alkyl diisocyanate, or wherein the organic isocyanate is an oligomeric or polymeric product obtained by reaction of the above diisocyanates with themselves and/or with a polyol.

6. The composition according to claim 1, wherein the organic isocyanate is a phenyl diisocyanate, diphenylmethane diisocyanate or naphthyl diisocyanate, each of which is unsubstituted or substituted by $C_1$-$C_4$ alkyl or di($C_1$-$C_4$ alkyl)amino, or wherein the organic isocyanate is an oligomeric or polymeric product obtained by reaction of the above diisocyanates with themselves and/or with a polyol.

7. The composition according to claim 1, wherein the organic isocyanate is a phenyl diisocyanate which is unsubstituted or substituted by $C_1$-$C_4$ alkyl, or wherein the organic isocyanate is an oligomeric or polymeric product obtained by reaction of the phenyl diisocyanate with itself and/or with a polyol.

8. The composition according to claim 5, wherein the polyol is a $C_1$-$C_{10}$ alkanol comprising two or more hydroxy groups, or wherein the polyol is a poly-$C_2$-$C_{10}$ alkylene glycol.

9. The composition according to claim 1, wherein R is $C_2$-$C_{40}$ alkyl which is uninterrupted or interrupted by —O—, —NH—, —S— and/or a carbonyl group.

10. The composition according to claim 1, wherein R is $C_8$-$C_{40}$ alkyl which is uninterrupted or interrupted by —O— and/or a carbonyl group.

11. The composition according to claim 1, wherein the polymeric substrate is a thermoplastic polymer.

12. The composition according to claim 1, wherein the polymeric substrate is a polyolefin selected from the group consisting of linear low density polyethylene, low density polyethylene, medium density polyethylene, high density polyethylene, a polyethylene copolymer, a polypropylene homopolymer, and a polypropylene copolymer.

13. The composition according to claim 1, further comprising at least one peroxide.

14. A fiber comprising the composition as defined in claim 1.

15. A nonwoven fabric prepared with multiple fibers according to claim 1.

16. A composition comprising:

a compound of formula (1) or (2)

(1)

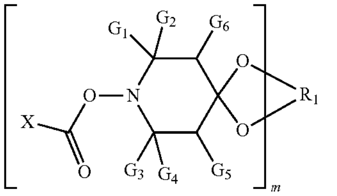

or (2)

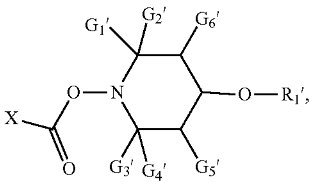

wherein $G_1$, $G_2$, $G_3$ and $G_4$ are each independently of each other $C_1$-$C_4$ alkyl, or $G_1$ and $G_2$ together or $G_3$ and $G_4$ together are pentamethylene;

$G_1$', $G_2$', $G_3$' and $G_4$' are each independently of each other $C_1$-$C_4$ alkyl, or $G_1$' and $G_2$' together or $G_3$' and $G_4$' together are pentamethylene;

$G_5$, $G_6$, $G_5$' and $G_6$' are each independently of each other hydrogen or $C_1$-$C_4$ alkyl; and X and X' are independently of each other hydrogen, $C_1$-$C_{18}$ alkyl, $C_2$-$C_{18}$ alkenyl, —O—$C_1$-$C_{18}$ alkyl, —NH—$C_1$-$C_{18}$ alkyl, —N($C_1$-$C_6$ alkyl)$_2$, phenyl, phenoxy or —NH-phenyl, m is 1 or 2, and when m is 1, $R_1$ is $C_2$-$C_8$ alkylene, $C_2$-$C_8$ hydroxy-alkylene or $C_4$-$C_{36}$ acyloxyalkylene, or when m is 2, $R_1$ is (—$CH_2$)$_2$C($CH_2$—)$_2$, and $R_1$' is hydrogen, $C_1$-$C_8$ alkyl, $C_1$-$C_8$ hydroxyalkyl or a group of formula —(C═O)—$C_1$-$C_{40}$ alkyl, or —O—$R_1$' together with a —CH— group linking them are a group —(C═O)—, and a compound of formula (3)

$$A-\!\!\left[S-R\right]_n, \quad (3)$$

wherein

A is based on an organic isocyanate, wherein radical(s) —S—R are introduced by reaction with isocyanate groups, R is $C_2$-$C_{40}$ alkyl which is optionally substituted and/or interrupted, and n is equal to or greater than 1.

17. A method of modifying the rheology of a polymeric substrate, the method comprising:

mixing the composition according to claim 16 with the polymeric substrate.

18. The composition according to claim 11, wherein the polymeric substrate is a polyolefin.

* * * * *